(12) United States Patent
Martinez Gil et al.

(10) Patent No.: US 9,796,687 B2
(45) Date of Patent: Oct. 24, 2017

(54) S-SUBSTITUTED QUINAZOLINES AND THEIR THERAPEUTIC APPLICATIONS FOR THE TREATMENT OF DISEASES MEDIATED BY PDE7

(71) Applicant: Consejo Superior De Investigaciones Cientificas (CSIC), Madrid (ES)

(72) Inventors: Ana Martinez Gil, Madrid (ES); Carmen Belen Gil Ayuso-Gontan, Talavera de la Reina (ES); Daniel Ignacio Perez Fernandez, Madrid (ES); Ana Maria Garcia Fernandez, Membrilla (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 0 days.

(21) Appl. No.: 15/157,060

(22) Filed: May 17, 2016

(65) Prior Publication Data

US 2016/0340320 A1    Nov. 24, 2016

(51) Int. Cl.
| | |
|---|---|
| *C07D 239/95* | (2006.01) |
| *C07D 401/12* | (2006.01) |
| *A61K 31/517* | (2006.01) |
| *C07D 239/91* | (2006.01) |

(52) U.S. Cl.
CPC .......... *C07D 239/95* (2013.01); *A61K 31/517* (2013.01); *C07D 239/91* (2013.01); *C07D 401/12* (2013.01)

(58) Field of Classification Search
CPC ............................ C07D 239/95; C07D 401/12
USPC .................................................... 514/266.21
See application file for complete search history.

(56) References Cited

FOREIGN PATENT DOCUMENTS

| | | |
|---|---|---|
| EP | 2 130 823 | 12/2009 |
| EP | 2 433 637 | 3/2012 |
| ES | 2308916 | 12/2008 |
| WO | WO 2008113881 | 9/2008 |
| WO | WO 2009/133379 | 11/2009 |
| WO | WO 2010/129036 | 11/2010 |
| WO | WO 2010133742 | 11/2010 |
| WO | WO 2013/025508 | 2/2013 |

OTHER PUBLICATIONS

Kottke et al. Pharmazie (1978), 33(1), p. 19-23.*
Rao et al. Indian Journal of Chemistry, Section B: Organic Chemistry including Medicinal Chemistry (1978), 16B(11), p. 1023-5.*
Rao, P.R. et al., "Synthesis & Antitubercular Activity of Some 2-Alkylthio-3-aryl-4(3H)-quinazolones," *Indian Journ. of Chem.* 16B: 1023-1025 (1978).
Junghänel, J. et la., "Circular Dichroism of Axially Chiral Methaqualone, 3-Aryl-2-Mercapto- and 3-Aryl-2-Alkylthio-4(3H)-Quinazolinones: Conformational Dependence of CD and Assignment of Absolute Configuration", *Chirality* 10: 253-261 (1998).
Redondo, M. et al., "Unraveling Phosphodiesterase Surfaces. Identification of Phosphodiesterase 2 Allosteric Modulation Cavities," *Euro. Journ. of Medicinal Chem.* 70:781-788 (2013).
Li, D. et al., "High Throughput Artificial Membrane Permeability Assay for Blood-Brain Barrier," *Euro. Journ. of Medicinal Chem.* 38:223-232 (2003).
Redondo, M. et al., "Neuroprotective Efficacy of Quinazoline Type Phosphodiesterase 7 Inhibitors in Cellular Cultures and Experimental Stroke Model," *Euro. Journ. of Medicinal Chem.* 47:175-185 (2012).
Search Report and Written Opinion Issued by the Spanish Patent Trademark Office in Spanish Patent Application No. 201530720, Aug. 20, 2015.
Anonymous: "AC10UC2H-C21H21FN20S", Pubchem, pp. 1-10, (2006).
Anonymous: "SID 67208835-ZINC27775011", Pubchem, pp. 1-6, (2009).
Database WPI, Week 201512, Thomson Scientific, XP002761922 and CN 104 151 300, *Medicine & Bioengineering Inst Chinese A*, (2014).
Johansson, Emily M., et al.: "Comparison of cAMP-specific phosphodiesterase mRNAs distribution in mouse and rat brain", Neuroscience Letters, vol. 525(1), pp. 1-6, (2012).
Kottke, K., et al.: "The preparation of 2-hydrazino-3-arylquinzolones-(4)—synthesis of compounds with an aminoguanidine structure", Die Pharmazie, vol. 33(1), pp. 19-23, (1978).
Shridhar, D. R., et al.: "Synthesis and pharmacology of some new methyl 4-[2-alkylthio-4(3H)-quinazolon-3-yl]phenylacetates", Journal of the Indian Chemical Society, vol. 62(9), pp. 687-689, (1985).
Extended European Search Report issued by the European Patent Office in European Patent Application No. 16166449.5, Sep. 27, 2016.

* cited by examiner

*Primary Examiner* — Yong Chu
(74) *Attorney, Agent, or Firm* — Seyfarth Shaw LLP (57) ABSTRACT

The present invention relates to a family of S-substituted quinazoline derivatives that inhibitors of the enzyme phosphodiesterase 7 (PDE7), useful for the treatment or prevention of diseases mediated by said enzyme, especially inflammatory, neurodegenerative, neurological, psychiatric and/or autoimmune diseases.

4 Claims, 2 Drawing Sheets

S-SUBSTITUTED QUINAZOLINES AND THEIR THERAPEUTIC APPLICATIONS FOR THE TREATMENT OF DISEASES MEDIATED BY PDE7

CROSS REFERENCE TO RELATED APPLICATIONS

This application claims priority to Spanish Patent Application No. 201530720, which was filed on May 22, 2015, the disclosure of which is incorporated herein by reference in its entirety.

The present invention relates to a family of S-substituted quinazoline derivatives that have selective or specific inhibitory activity of the enzyme phosphodiesterase 7 (PDE7), without significantly inhibiting other phosphodiesterases such as the enzyme phosphodiesterase 4 (PDE4). The S-substituted quinazoline derivatives of the present invention are, therefore, useful for the treatment or prevention of diseases mediated by said enzyme PDE7, especially inflammatory, neurodegenerative, neurological, psychiatric and/or autoimmune diseases. Consequently, the invention could have applications in the fields of pharmaceutical chemistry and pharmacology.

The phosphodiesterases (PDEs) are a family of metal-dependent phosphohydrolase enzymes that metabolise the second messengers adenosine 3',5'-cyclic monophosphate and guanosine 3',5'-cyclic monophosphate (cAMP and cGMP) to their respective 5'-monophosphates. cAMP and cGMP are mediators in the action of hormones, neurotransmitters and other cellular effectors involved in many physiological processes. Taking into account that the increase in cAMP levels has an important impact on immunosuppressive and anti-inflammatory properties, selective inhibitors of PDEs have been widely studied for the treatment of certain pathologies such as immunological disorders, inflammatory processes and disorders of the central nervous system.

Patent application PCT WO2008/113881 discloses a family of compounds with a quinazoline nucleus that have dual inhibitory activity of enzymes PDE7 and PDE4 and are useful for the treatment of inflammatory or autoimmune diseases.

Patent application PCT WO2010/133742 discloses that the compounds with a quinazoline nucleus described in patent application WO2008/113881 are useful for the treatment of neurodegenerative and/or neurological diseases.

Given the physiological importance of the routes via which the PDEs operate, it is of interest to find selective and effective inhibitors of these enzymes that have good pharmacological properties in relation to administration, distribution, metabolism and excretion, and that, moreover, do not have any secondary or adverse effects, or such secondary or adverse effects are diminished or reduced with respect to what is observed for the compounds of the state of the art.

The inventors of the present patent, after extensive and exhaustive research, have surprisingly discovered a family of S-substituted quinazoline derivatives that have selective or specific inhibitory activity of the enzyme phosphodiesterase 7 (PDE7), without significantly inhibiting other phosphodiesterases such as the enzyme phosphodiesterase 4 (PDE4). The family of compounds discovered by the inventors of the present patent are, therefore, useful for the treatment or prevention of diseases mediated by said enzyme PDE7, especially inflammatory, neurodegenerative, neurological, psychiatric and/or autoimmune diseases. Moreover, since they selectively inhibit enzyme PDE7 without affecting other phosphodiesterases (for example, PDE4), the compounds of this family have improved pharmacological and pharmacokinetic properties (for example, improved permeability across the blood-brain barrier) and fewer or no secondary effects (normally associated with inhibitory action in enzyme PDE4), compared with other compounds with a quinazoline nucleus known in the state of the art that have inhibitory activity of both PDE4 and PDE7 (dual inhibitory action).

The term "alkyl", as used in the present document, refers to radicals of hydrocarbon chains, linear or branched, that have from 1 to 10 carbon atoms, preferably from 1 to 6, and more preferably from 1 to 4, and that bind to the rest of the molecule by a single bond, for example, methyl, ethyl, n-propyl, i-propyl, n-butyl, tert-butyl, sec-butyl, n-pentyl, n-hexyl, etc. The alkyl groups can be optionally substituted by one or more substituents such as halo, hydroxy, alkoxy, carboxy, carbonyl, cyano, acyl, alkoxycarbonyl, amino, nitro, mercapto and alkylthio.

The term "cycloalkyl", as used in the present document, refers to a stable monocyclic or bicyclic radical with 3 to 10 members, preferably from 3 to 8 members, and more preferably from 3 to 6 members, that is saturated or partially saturated and consists solely of carbon and hydrogen atoms, such as cyclopentyl, cyclohexyl and adamantyl, and that can be optionally substituted by one or more groups such as alkyl, halo, hydroxyl, alkoxy, carboxy, cyano, carbonyl, acyl, alkoxycarbonyl, amino, nitro, mercapto and alkylthio.

The term "aryl", as used in the present document, refers to an aromatic carbocyclic chain that has from 6 to 18 carbon atoms, preferably from 6 to 14 carbon atoms, and more preferably from 6 to 8, and can be single- or multiple-ring, in the latter case with separated and/or condensed rings. Non-limitative examples of aryl groups are, for example, phenyl, naphthyl or indenyl. Preferably, the aryl group is a phenyl or a naphthyl. The aryl groups can optionally be substituted by one or more substituents such as halo, hydroxyl, alkoxy, carboxy, carbonyl, cyano, acyl, alkoxycarbonyl, amino, nitro, mercapto and alkylthio.

The term "heteroaryl", as used in the present document, refers to a stable monocyclic or bicyclic radical with 3 to 15 members that is unsaturated, saturated or partially saturated and that consists of carbon atoms and at least one heteroatom selected from nitrogen, oxygen or sulphur. Preferably it has from 4 to 8 members with one or more heteroatoms, and more preferably from 5 to 6 members with one or more heteroatoms. Non-limitative examples of heterocycles can be, for example, azepines, indoles, imidazoles, isothiazoles, thiadiazoles, furan, tetrahydrofuran, benzymidazole, benzothiazole, piperidinyl, piperazinyl, purine or quinoline. In the most preferred embodiment, the heteroaryl group is pyridine. The heteroaryl groups can optionally be substituted by one or more substituents such as halo, hydroxyl, alkoxy, carboxy, carbonyl, cyano, acyl, alkoxycarbonyl, amino, nitro, mercapto and alkylthio.

The terms "halo" or "halogen", as used in the present document, refer to fluorine, chlorine, bromine or iodine, and its anions are referred to as halides.

As used in the present document, the term "prodrug" and its plurals refer to esters, including carboxylic acid esters, amino acid esters, phosphate esters, sulphonate esters of metal salts, etc., carbamates, amides, etc., which, when administered to an individual, are capable of providing, directly or indirectly, the compound of interest in said individual. Advantageously, a "prodrug" is a compound that increases the bioavailability of the compound of interest when administered to an individual or that enhances the release of the compound of interest in a biological compartment. The preparation of said "prodrug" can be carried out by conventional methods known to a person skilled in the art.

As used in the present document, the term "derivative" and its plurals refer both to pharmaceutically acceptable compounds, i.e. derived from the compound of interest, that can be used in the preparation of a drug, and to pharmaceutically unacceptable derivatives since these may be useful in the preparation of pharmaceutically acceptable derivatives.

As used in the present document, the term "salt" and its plurals refer to any type of salt from among those known in the state of the art, for example, halide salts, hydroxy acid salts (such as oxyacid salts, acid salts, basic salts and double salts), hydroxo salts, mixed salts, oxy salts or other hydrated salts. This term comprises both pharmaceutically acceptable salts and pharmaceutically unacceptable salts, since the latter may be useful in the preparation of pharmaceutically acceptable salts.

As used in the present document, the term "isomer" and its plurals refer to optical isomers, enantiomers, stereoisomers or diastereoisomers. The individual enantiomers or diastereoisomers, as well as their mixtures, may be separated by conventional techniques known in the state of the art.

As used in the present document, the term "solvate" and its plurals refer to any solvate known in the state of the art, such as polar, apolar or amphiphilic solvates, and include any pharmaceutically acceptable solvate which, when administered to a patient (directly or indirectly) provides the compound of interest (the compound of the present invention). Preferably, the solvate is a hydrate, a solvate with an alcohol such as methanol, ethanol, propanol or isopropanol, a solvate with an ester such as ethyl acetate, a solvate with an ether such as methyl ether, ethyl ether or THF (tetrahydrofuran) or a solvate with DMF (dimethylformamide), and more preferably a hydrate or a solvate with an alcohol such as ethanol.

As used in the present document, the expression "therapeutically effective quantity" refers to the quantity of administered compound sufficient to produce the desired effect in such a way that the symptoms of the disease are diminished. The dosage must not be used in proportions or at levels that cause undesired collateral or secondary effects whose clinical assessment renders them adverse and not treatable therapeutically. In general, the "therapeutically effective quantity" will vary according to the patient's age, condition and sex, as well as the advancement of the disease and the route and frequency of administration, and can be determined in each case by the person skilled in the art.

In a first aspect, the present invention relates to the use of a composition that comprises a compound of formula (I):

(I)

where m is selected from 0 to 4 and n is selected from 0 to 5,
X is selected from S or O,
$R_1$ and $R_2$ are selected independently from substituted or unsubstituted $C_1$-$C_6$ alkyl or halogen, and $R_3$ is selected from substituted or unsubstituted $C_1$-$C_6$ alkyl, substituted or unsubstituted $C_3$-$C_6$ cycloalkyl, substituted or unsubstituted aryl or substituted or unsubstituted heteroaryl,
or their isomers, salts, derivatives, prodrugs or pharmaceutically acceptable solvates, for the manufacture of a medicament for the treatment and/or prevention of a disease mediated by the enzyme phosphodiesterase 7.

In a preferred embodiment, said disease mediated by the enzyme phosphodiesterase 7 is an inflammatory, neurodegenerative, neurological, psychiatric and/or autoimmune disease.

In a preferred embodiment, X is O.
In a preferred embodiment, m is 0 or 1, and still more preferably m is 0.
In a preferred embodiment, $R_1$ is at position 8 of the quinazoline ring.
In a preferred embodiment, $R_1$ is halogen and, more preferably, $R_1$ is chlorine.
In another preferred embodiment, $R_1$ is $C_1$-$C_4$ alkyl and, more preferably, $R_1$ is methyl.
In a preferred embodiment, n is 0, 1 or 2. In the most preferred embodiment, n is 0.
In a preferred embodiment, $R_2$ is at position 2 of the phenyl ring.
In another preferred embodiment, $R_2$ is at positions 2 and 6 of the phenyl ring.
In another preferred embodiment, $R_2$ is halogen and, more preferably, $R_2$ is selected from fluorine and bromine.
In another preferred embodiment, $R_2$ is $C_1$-$C_4$ alkyl and, more preferably, $R_2$ is methyl.
In a preferred embodiment, $R_3$ is aryl and, more preferably, $R_3$ is selected from phenyl or 2-naphthyl.
In another preferred embodiment, $R_3$ is $C_1$-$C_4$ alkyl and, more preferably, $R_3$ is selected from methyl or tert-butyl.
In another preferred embodiment, $R_3$ is $C_3$-$C_6$ cycloalkyl and, more preferably, $R_3$ is selected from cyclopropyl or cyclohexyl.
In another preferred embodiment, $R_3$ is heteroaryl and, more preferably, $R_3$ is selected from 2-pyridinyl, 3-pyridinyl or 4-pyridinyl.
In a preferred embodiment, the compound of formula (I) for the manufacture of a medicament is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
3-(2,6-Difluorophenyl)-8-methyl-2-neopentylthio-4-oxo-3,4-dihydroquinazoline (comp. 6)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-phenyl-4-oxo-3,4-dihydroquinazoline (comp. 16)
2-Ethylthio-3-(2,6-difluorophenyl)-4-oxo-3,4-dihydroquinazoline (comp. 17)
8-Chloro-2-ethylthio-3-(2,6-difluorophenyl)-4-oxo-3,4-dihydroquinazoline (comp. 18)
2-Ethylthio-3-(4-fluorophenyl)-4-oxo-3,4-dihydroquinazoline (comp. 19)

2-Benzylthio-3-phenyl-4-oxo-3,4-dihydroquinazoline (comp. 21)
3-Phenyl-2-(2-pyridylmethylthio)-4-oxo-3,4-dihydroquinazoline (comp. 23)
3-Phenyl-2-(3-pyridylmethylthio)-4-oxo-3,4-dihydroquinazoline (comp. 24)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)
3-Phenyl-2-(4-pyridylmethylthio)-4-oxo-3,4-dihydroquinazoline (comp. 27)
3-Phenyl-2-(2-naphthylmethylthio)-4-oxo-3,4-dihydroquinazoline (comp. 28)

In a more preferred embodiment, the compound of formula (I) for the manufacture of a medicament is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
8-Chloro-2-ethylthio-3-(2,6-difluorophenyl)-4-oxo-3,4-dihydroquinazoline (comp. 18)
2-Benzylthio-3-phenyl-4-oxo-3,4-dihydroquinazoline (comp. 21)
3-Phenyl-2-(2-pyridylmethylthio)-4-oxo-3,4-dihydroquinazoline (comp. 23)
3-Phenyl-2-(3-pyridylmethylthio)-4-oxo-3,4-dihydroquinazoline (comp. 24)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)
3-Phenyl-2-(4-pyridylmethylthio)-4-oxo-3,4-dihydroquinazoline (comp. 27)
3-Phenyl-2-(2-naphthylmethylthio)-4-oxo-3,4-dihydroquinazoline (comp. 28)

In the most preferred embodiment, the compound of formula (I) for the manufacture of a medicament is 3-Phenyl-2-neopentylthio-4-oxo-3,4-dihydroquinazoline (comp. 5)

In another preferred embodiment, the compound of formula (I) is a compound of formula (II):

(II)

where $R_4$, $R_5$ and $R_6$ are selected independently from hydrogen, substituted or unsubstituted $C_1$-$C_4$ alkyl or halogen, and $R_7$ is selected from substituted or unsubstituted $C_3$-$C_6$ cycloalkyl, substituted or unsubstituted $C_1$-$C_4$ alkyl or 3-pyridinyl, with the condition that when $R_7$ is methyl or 3-pyridinyl, R5 or R6 are not hydrogen, or their isomers, salts, derivatives, prodrugs or pharmaceutically acceptable solvates.

In a preferred embodiment, $R_4$ is $C_1$-$C_4$ alkyl and, more preferably, methyl.
In another preferred embodiment, $R_4$ is halogen and, more preferably, chlorine.
In another preferred embodiment, $R_5$ is $C_1$-$C_4$ alkyl and, more preferably, methyl.
In another preferred embodiment, $R_5$ is halogen and, more preferably, selected from fluorine or bromine.
In another preferred embodiment, $R_6$ is halogen and, more preferably, fluorine.
In another preferred embodiment, $R_7$ is $C_3$-$C_6$ cycloalkyl and, more preferably, is selected from cyclohexyl or cyclopropyl.
In another preferred embodiment, $R_7$ is $C_1$-$C_4$ alkyl and, more preferably, is selected from methyl or tert-butyl.
In another preferred embodiment, $R_7$ is 3-pyridinyl.
In another preferred embodiment, the compound of formula (II) is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
3-(2,6-Difluorophenyl)-8-methyl-2-neopentylthio-4-oxo-3,4-dihydroquinazoline (comp. 6)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-(2,6-difluorophenyl)-4-oxo-3,4-dihydroquinazoline (comp. 17)
8-Chloro-2-ethylthio-3-(2,6-difluorophenyl)-4-oxo-3,4-dihydroquinazoline (comp. 18)
2-Ethylthio-3-(4-fluorophenyl)-4-oxo-3,4-dihydroquinazoline (comp. 19)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)

In the most preferred embodiment, the compound of formula (II) is 3-Phenyl-2-neopentylthio-4-oxo-3,4-dihydroquinazoline (comp. 5)

Unless indicated otherwise, the compounds of the present invention also include compounds that differ only in the presence of one or more isotopically enriched atoms. For example, compounds that have said structure except for the substitution of a hydrogen atom with a deuterium or tritium atom, or the substitution of a carbon atom with a $^{13}$C- or $^{14}$C-enriched carbon atom or a $^{15}$N-enriched nitrogen atom.

The compounds of formula (I) or (II) for therapeutic use are prepared in solid form or in aqueous suspension, in a pharmaceutically acceptable diluent. These preparations may be administered by any appropriate route of administration known in the state of the art, for which purpose said preparation will be formulated in the pharmaceutical form appropriate to the corresponding route of administration chosen. In a preferred embodiment, the route of administration of the compound of formula (I) or (II) of the present invention is oral, topical, rectal or parenteral (including subcutaneous, intraperitoneal, intradermal, intramuscular, intravenous, etc.). A review of the different pharmaceutical forms of administration of drugs and of the excipients necessary for obtaining the same can be found, for example, in "Tratado de Farmacia Galénica", C. Faulí i Trillo, 1993, Luzán 5, S.A. Ediciones, Madrid, or in other regular or similar publications of the Spanish Pharmacopoeia and in the United States.

The compounds described in the present invention, their isomers, salts, derivatives, prodrugs or pharmaceutically acceptable solvates, as well as the pharmaceutical compositions that contain them, can be used together or in combination with other additional drugs in order to provide a combination therapy. Said additional drugs may form part of the same pharmaceutical composition, or alternatively, may be provided in the form of a separate composition for administration simultaneously or non-simultaneously with the pharmaceutical composition that comprises a compound of formula (I) or (II), or an isomer, salt, derivative, prodrug or pharmaceutically acceptable solvate thereof.

It is envisaged that the composition is a pharmaceutical composition. In a preferred embodiment, the pharmaceutical composition further comprises another active principle. The use of the compounds of the invention is compatible with protocols in which the compounds of the formula (I) or (II) or their mixtures are used by themselves or in combination with other treatments or any medical procedure.

In a preferred embodiment, the disease mediated by the enzyme phosphodiesterase 7 is an inflammatory or autoimmune disease selected from intestinal inflammatory disease, inflammatory articular pathologies, atopical dermatitis and other inflammatory dermatological pathologies, neuritis, encephalitis, encephalomielitis, and inflammatory pathologies that affect the central nervous systems (multiple sclerosis) or the peripheral nervous system, myositis, vasculitis, systemic lupus erythematosus, asthma, chronic obstructive pulmonary disease, infectious diseases that involve inflammation, or combinations thereof.

In another preferred embodiment, the disease mediated by the enzyme phosphodiesterase 7 is a neurodegenerative or neurological disease selected from Alzheimer's disease, Parkinson's disease, amyotrophic lateral sclerosis, cerebral ischaemia, post-encephalitic Parkinsonism, dystonias, Tourette's syndrome, periodic limb movement disorder, restless leg syndrome, epilepsy, or combinations thereof.

In another preferred embodiment, the disease mediated by the enzyme phosphodiesterase 7 is a psychiatric disease selected from psychotic disorders, schizophrenia, depression, bipolar disorder, attention deficit disorder, or combinations thereof.

In the most preferred embodiment, the disease mediated by the enzyme phosphodiesterase 7 is a neurodegenerative disease, and still more preferably, said disease is Alzheimer's disease or Parkinson's disease.

Another aspect of the invention relates to the composition that comprises the compound of formula (I):

(I)

where m is selected from 0 to 4 and n is selected from 0 to 5,
X is selected from S or O,
$R_1$ and $R_2$ are selected independently from substituted or unsubstituted $C_1$-$C_6$ alkyl or halogen, and
$R_3$ is selected from substituted or unsubstituted $C_1$-$C_6$ alkyl, substituted or unsubstituted $C_3$-$C_6$ cycloalkyl, substituted or unsubstituted aryl or substituted or unsubstituted heteroaryl,
or their isomers, salts, derivatives, prodrugs or pharmaceutically acceptable solvates.
for their use in the treatment of a disease mediated by PDE7.

In a preferred embodiment, said disease mediated by the enzyme phosphodiesterase 7 is an inflammatory, neurodegenerative, neurological, psychiatric and/or autoimmune disease.

In a preferred embodiment, X is O.

In a preferred embodiment, m is 0 or 1, and still more preferably m is 0.

In a preferred embodiment, $R_1$ is at position 8 of the quinazoline ring.

In a preferred embodiment, $R_1$ is halogen and, more preferably, $R_1$ is chlorine.

In another preferred embodiment, $R_1$ is $C_1$-$C_4$ alkyl and, more preferably, $R_1$ is methyl.

In a preferred embodiment, n is 0, 1 or 2. In the most preferred embodiment, n is 0.

In a preferred embodiment, $R_2$ is at position 2 of the phenyl ring.

In another preferred embodiment, $R_2$ is at positions 2 and 6 of the phenyl ring.

In another preferred embodiment, $R_2$ is halogen and, more preferably, $R_2$ is selected from fluorine and bromine.

In another preferred embodiment, $R_2$ is $C_1$-$C_4$ alkyl and, more preferably, $R_2$ is methyl.

In a preferred embodiment, $R_3$ is aryl and, more preferably, $R_3$ is selected from phenyl or 2-naphthyl.

In another preferred embodiment, $R_3$ is $C_1$-$C_4$ alkyl and, more preferably, $R_3$ is selected from methyl or tert-butyl.

In another preferred embodiment, $R_3$ is $C_3$-$C_6$ cycloalkyl and, more preferably, $R_3$ is selected from cyclopropyl or cyclohexyl.

In another preferred embodiment, $R_3$ is heteroaryl and, more preferably, $R_3$ is selected from 2-pyridinyl, 3-pyridinyl or 4-pyridinyl.

In a preferred embodiment, the compound of formula (I) is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
3-(2,6-Difluorophenyl)-8-methyl-2-neopentylthio-4-oxo-3,4-dihydroquinazoline (comp. 6)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-phenyl-4-oxo-3,4-dihydroquinazoline (comp. 16)
2-Ethylthio-3-(2,6-difluorophenyl)-4-oxo-3,4-dihydroquinazoline (comp. 17)

8-Chloro-2-ethylthio-3-(2,6-difluorophenyl)-4-oxo-3,4-dihydroquinazoline (comp. 18)
2-Ethylthio-3-(4-fluorophenyl)-4-oxo-3,4-dihydroquinazoline (comp. 19)
2-Benzylthio-3-phenyl-4-oxo-3,4-dihydroquinazoline (comp. 21)
3-Phenyl-2-(2-pyridylmethylthio)-4-oxo-3,4-dihydroquinazoline (comp. 23)
3-Phenyl-2-(3-pyridylmethylthio)-4-oxo-3,4-dihydroquinazoline (comp. 24)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)
3-Phenyl-2-(4-pyridylmethylthio)-4-oxo-3,4-dihydroquinazoline (comp. 27)
3-Phenyl-2-(2-naphthylmethylthio)-4-oxo-3,4-dihydroquinazoline (comp. 28)

In a more preferred embodiment, the compound of formula (I) is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
8-Chloro-2-ethylthio-3-(2,6-difluorophenyl)-4-oxo-3,4-dihydroquinazoline (comp. 18)
2-Benzylthio-3-phenyl-4-oxo-3,4-dihydroquinazoline (comp. 21)
3-Phenyl-2-(2-pyridylmethylthio)-4-oxo-3,4-dihydroquinazoline (comp. 23)
3-Phenyl-2-(3-pyridylmethylthio)-4-oxo-3,4-dihydroquinazoline (comp. 24)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)
3-Phenyl-2-(4-pyridylmethylthio)-4-oxo-3,4-dihydroquinazoline (comp. 27)
3-Phenyl-2-(2-naphthylmethylthio)-4-oxo-3,4-dihydroquinazoline (comp. 28)

In the most preferred embodiment, the compound of formula (I) is 3-Phenyl-2-neopentylthio-4-oxo-3,4-dihydroquinazoline (comp. 5)

In another preferred embodiment, the compound of formula (I) is a compound of formula (II):

(II)

where $R_4$, $R_5$ y $R_6$ are selected independently from hydrogen, substituted or unsubstituted $C_1$-$C_4$ alkyl or halogen, and $R_7$ is selected from substituted or unsubstituted $C_3$-$C_6$ cycloalkyl, substituted or unsubstituted $C_1$-$C_4$ alkyl or 3-pyridinyl,
with the condition that, when $R_7$ is methyl or 3-pyridinyl, $R_5$ or $R_6$ are not hydrogen,
or their isomers, salts, derivatives, prodrugs or pharmaceutically acceptable solvates.

In a preferred embodiment, $R_4$ is $C_1$-$C_4$ alkyl and, more preferably, methyl.
In another preferred embodiment, $R_4$ is halogen and, more preferably, chlorine.
In a preferred embodiment, $R_5$ is $C_1$-$C_4$ alkyl and, more preferably, methyl.
In another preferred embodiment, $R_5$ is halogen and, more preferably, selected from fluorine or bromine.
In another preferred embodiment, $R_6$ is halogen and, more preferably, fluorine.
In another preferred embodiment, $R_7$ is $C_3$-$C_6$ cycloalkyl and, more preferably, is selected from cyclohexyl or cyclopropyl.
In another preferred embodiment, $R_7$ is $C_1$-$C_4$ alkyl and, more preferably, is selected from methyl or tert-butyl.
In another preferred embodiment, $R_7$ is 3-pyridinyl.
In another preferred embodiment, the compound of formula (II) is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
3-(2,6-Difluorophenyl)-8-methyl-2-neopentylthio-4-oxo-3,4-dihydroquinazoline (comp. 6)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-(2,6-difluorophenyl)-4-oxo-3,4-dihydroquinazoline (comp. 17)
8-Chloro-2-ethylthio-3-(2,6-difluorophenyl)-4-oxo-3,4-dihydroquinazoline (comp. 18)
2-Ethylthio-3-(4-fluorophenyl)-4-oxo-3,4-dihydroquinazoline (comp. 19)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)

In the most preferred embodiment, the compound of formula (II) is 3-Phenyl-2-neopentylthio-4-oxo-3,4-dihydroquinazoline (comp. 5)

Unless indicated otherwise, the compounds of the present invention also include compounds that differ only in the presence of one or more isotopically enriched atoms. For example, compounds that have said structure except for the substitution of a hydrogen atom with a deuterium or tritium atom, or the substitution of a carbon atom with a $^{13}$C- or $^{14}$C-enriched carbon atom or a $^{15}$N-enriched nitrogen atom.

The compounds of formula (I) or (II) for therapeutic use are prepared in solid form or in aqueous suspension, in a pharmaceutically acceptable diluent. These preparations may be administered by any appropriate route of administration known in the state of the art, for which purpose said preparation will be formulated in the pharmaceutical form appropriate to the corresponding route of administration chosen. In a preferred embodiment, the route of administration of the compound of formula (I) or (II) of the present invention is oral, topical, rectal or parenteral (including subcutaneous, intraperitoneal, intradermal, intramuscular, intravenous, etc.). A review of the different pharmaceutical forms of administration of drugs and of the excipients necessary for obtaining the same can be found, for example, in "Tratado de Farmacia Galénica", C. Faulí i Trillo, 1993, Luzán 5, S.A. Ediciones, Madrid, or in other regular or similar publications of the Spanish Pharmacopoeia and in the United States.

The compounds described in the present invention, their isomers, salts, derivatives, prodrugs or pharmaceutically acceptable solvates, as well as the pharmaceutical compositions that contain them, can be used together or in combination with other additional drugs in order to provide a combination therapy. Said additional drugs may form part of the same pharmaceutical composition, or alternatively may be provided in the form of a separate composition for administration simultaneously or non-simultaneously with the pharmaceutical composition that comprises a compound of formula (I) or (II), or an isomer, salt, derivative, prodrug or pharmaceutically acceptable solvate thereof.

It is envisaged that the composition is a pharmaceutical composition. In a preferred embodiment, the pharmaceutical composition further comprises another active principle. The use of the compounds of the invention is compatible with protocols in which the compounds of the formula (I) or (II) or their mixtures are used by themselves or in combination with other treatments or any medical procedures.

In a preferred embodiment, the disease mediated by the enzyme phosphodiesterase 7 is an inflammatory or autoimmune disease selected from intestinal inflammatory disease, inflammatory articular pathologies, atopical dermatitis and other inflammatory dermatological pathologies, neuritis, encephalitis, encephalomielitis, and inflammatory pathologies that affect the central nervous systems (multiple sclerosis) or the peripheral nervous system, myositis, vasculitis, systemic lupus erythematosus, asthma, chronic obstructive pulmonary disease, infectious diseases that involve inflammation, or combinations thereof.

In another preferred embodiment, the disease mediated by the enzyme phosphodiesterase 7 is a neurodegenerative or neurological disease selected from Alzheimer's disease, Parkinson's disease, amyotrophic lateral sclerosis, cerebral ischaemia, post-encephalitic Parkinsonism, dystonias, Tourette's syndrome, periodic limb movement disorder, restless leg syndrome, epilepsy, or combinations thereof.

In another preferred embodiment, the disease mediated by the enzyme phosphodiesterase 7 is a psychiatric disease selected from psychotic disorders, schizophrenia, depression, bipolar disorder, attention deficit disorder, or combinations thereof.

In the most preferred embodiment, the disease mediated by the enzyme phosphodiesterase 7 is a neurodegenerative disease, and still more preferably, said disease is Alzheimer's disease or Parkinson's disease.

Another aspect of the invention relates to a method for treating a disease mediated by PDE7 in a patient in need of such treatment, said method comprising the administration of a therapeutically effective quantity of a composition that comprises a compound of formula (I):

where m is selected from 0 to 4 and n is selected from 0 to 5,

X is selected from S or O, $R_1$ and $R_2$ are selected independently from substituted or unsubstituted $C_1$-$C_6$ alkyl or halogen, and $R_3$ is selected from substituted or unsubstituted $C_1$-$C_6$ alkyl, substituted or unsubstituted $C_3$-$C_6$ cycloalkyl, substituted or unsubstituted aryl or substituted or unsubstituted heteroaryl, or their isomers, salts, derivatives, prodrugs or pharmaceutically acceptable solvates.

In a preferred embodiment, said disease mediated by the enzyme phosphodiesterase 7 is an inflammatory, neurodegenerative, neurological, psychiatric and/or autoimmune disease.

In a preferred embodiment, X is O.

In a preferred embodiment, m is 0 or 1, and still more preferably m is 0.

In a preferred embodiment, $R_1$ is at position 8 of the quinazoline ring.

In a preferred embodiment, $R_1$ is halogen and, more preferably, $R_1$ is chlorine.

In another preferred embodiment, $R_1$ is $C_1$-$C_4$ alkyl and, more preferably, $R_1$ is methyl.

In a preferred embodiment, n is 0, 1 or 2. In the most preferred embodiment, n is 0.

In a preferred embodiment, $R_2$ is at position 2 of the phenyl ring.

In another preferred embodiment, $R_2$ is at positions 2 and 6 of the phenyl ring.

In another preferred embodiment, $R_2$ is halogen and, more preferably, $R_2$ is selected from fluorine and bromine.

In another preferred embodiment, $R_2$ is $C_1$-$C_4$ alkyl and, more preferably, $R_2$ is methyl.

In a preferred embodiment, $R_3$ is aryl and, more preferably, $R_3$ is selected from phenyl or 2-naphthyl.

In another preferred embodiment, $R_3$ is $C_1$-$C_4$ alkyl and, more preferably, $R_3$ is selected from methyl or tert-butyl.

In another preferred embodiment, $R_3$ is $C_3$-$C_6$ cycloalkyl and, more preferably, $R_3$ is selected from cyclopropyl or cyclohexyl.

In another preferred embodiment, $R_3$ is heteroaryl and, more preferably, $R_3$ is selected from 2-pyridinyl, 3-pyridinyl or 4-pyridinyl.

In a preferred embodiment, the compound of formula (I) in the treatment method of the present invention is selected from:

2-Cyclohexylmethylthio-3-phenyl-4-oxo-3,4-dihydroquinazoline (comp. 1)

3-(2-Bromophenyl)-2-cyclohexylmethylthio-4-oxo-3,4-dihydroquinazoline (comp. 2)

3-Phenyl-2-neopentylthio-4-oxo-3,4-dihydroquinazoline (comp. 5)

3-(2,6-Difluorophenyl)-8-methyl-2-neopentylthio-4-oxo-3,4-dihydroquinazoline (comp. 6)

8-Chloro-3-phenyl-2-neopentylthio-4-oxo-3,4-dihydroquinazoline (comp. 11)

3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-phenyl-4-oxo-3,4-dihydroquinazoline (comp. 16)
2-Ethylthio-3-(2,6-difluorophenyl)-4-oxo-3,4-dihydroquinazoline (comp. 17)
8-Chloro-2-ethylthio-3-(2,6-difluorophenyl)-4-oxo-3,4-dihydroquinazoline (comp. 18)
2-Ethylthio-3-(4-fluorophenyl)-4-oxo-3,4-dihydroquinazoline (comp. 19)
2-Benzylthio-3-phenyl-4-oxo-3,4-dihydroquinazoline (comp. 21)
3-Phenyl-2-(2-pyridylmethylthio)-4-oxo-3,4-dihydroquinazoline (comp. 23)
3-Phenyl-2-(3-pyridylmethylthio)-4-oxo-3,4-dihydroquinazoline (comp. 24)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)
3-Phenyl-2-(4-pyridylmethylthio)-4-oxo-3,4-dihydroquinazoline (comp. 27)
3-Phenyl-2-(2-naphthylmethylthio)-4-oxo-3,4-dihydroquinazoline (comp. 28)

In a more preferred embodiment, the compound of formula (I) in the treatment method of the present invention is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
8-Chloro-2-ethylthio-3-(2,6-difluorophenyl)-4-oxo-3,4-dihydroquinazoline (comp. 18)
2-Benzylthio-3-phenyl-4-oxo-3,4-dihydroquinazoline (comp. 21)
3-Phenyl-2-(2-pyridylmethylthio)-4-oxo-3,4-dihydroquinazoline (comp. 23)
3-Phenyl-2-(3-pyridylmethylthio)-4-oxo-3,4-dihydroquinazoline (comp. 24)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)
3-Phenyl-2-(4-pyridylmethylthio)-4-oxo-3,4-dihydroquinazoline (comp. 27)
3-Phenyl-2-(2-naphthylmethylthio)-4-oxo-3,4-dihydroquinazoline (comp. 28)

In the most preferred embodiment, the compound of formula (I) in the treatment method of the present invention is 3-Phenyl-2-neopentylthio-4-oxo-3,4-dihydroquinazoline (comp. 5)

In another preferred embodiment, the compound of formula (I) is a compound of formula (II):

where $R_4$, $R_5$ y $R_6$ are selected independently from hydrogen, substituted or unsubstituted $C_1$-$C_4$ alkyl or halogen, and $R_7$ is selected from substituted or unsubstituted $C_3$-$C_6$ cycloalkyl, substituted or unsubstituted $C_1$-$C_4$ alkyl or 3-pyridinyl, with the condition that when $R_7$ is methyl or 3-pyridinyl, $R_5$ or $R_6$ are not hydrogen,
or their isomers, salts, derivatives, prodrugs or pharmaceutically acceptable solvates.

In a preferred embodiment, $R_4$ is $C_1$-$C_4$ alkyl and, more preferably, methyl.

In another preferred embodiment, $R_4$ is halogen and, more preferably, chlorine.

In another preferred embodiment, $R_5$ is $C_1$-$C_4$ alkyl and, more preferably, methyl.

In another preferred embodiment, $R_5$ is halogen and, more preferably, is selected from fluorine or bromine.

In another preferred embodiment, $R_6$ is halogen and, more preferably, fluorine.

In another preferred embodiment, $R_7$ is $C_3$-$C_6$ cycloalkyl and, more preferably, is selected from cyclohexyl or cyclopropyl.

In another preferred embodiment, $R_7$ is $C_1$-$C_4$ alkyl and, more preferably, is selected from methyl or tert-butyl.

In another preferred embodiment, $R_7$ is 3-pyridinyl.

In another preferred embodiment, the compound of formula (II) is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
3-(2,6-Difluorophenyl)-8-methyl-2-neopentylthio-4-oxo-3,4-dihydroquinazoline (comp. 6)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-(2,6-difluorophenyl)-4-oxo-3,4-dihydroquinazoline (comp. 17)
8-Chloro-2-ethylthio-3-(2,6-difluorophenyl)-4-oxo-3,4-dihydroquinazoline (comp. 18)
2-Ethylthio-3-(4-fluorophenyl)-4-oxo-3,4-dihydroquinazoline (comp. 19)
8-Chloro-2-(3-pyridylmethylthio)-4-oxo-3,4-dihydroquinazoline (comp. 25)
3-(2-Methylphenyl)-2-(3-pyridylmethylthio)-4-oxo-3,4-dihydroquinazoline (comp. 26)

In the most preferred embodiment, the compound of formula (II) is 3-Phenyl-2-neopentylthio-4-oxo-3,4-dihydroquinazoline (comp. 5)

Unless indicated otherwise, the compounds of the present invention also include compounds that differ only in the presence of one or more isotopically enriched atoms. For example, compounds that have said structure except for the substitution of a hydrogen atom with a deuterium or tritium atom, or the substitution of a carbon atom with a $^{13}$C- or $^{14}$C-enriched carbon atom or a $^{15}$N-enriched nitrogen atom.

The compounds of formula (I) or (II) for use in the method of the present invention are prepared in solid form or in aqueous suspension, in a pharmaceutically acceptable diluent. These preparations may be administered by any appropriate route of administration known in the state of the art, for which purpose said preparation will be formulated in the pharmaceutical form appropriate to the corresponding route of administration chosen. In a preferred embodiment, the route of administration of the compound of formula (I) or (II) of the present invention is oral, topical, rectal or parenteral (including subcutaneous, intraperitoneal, intradermal, intramuscular, intravenous, etc.). A review of the different pharmaceutical forms of administration of drugs and of the excipients necessary for obtaining the same can be found, for example, in "Tratado de Farmacia Galénica", C. Faulí i Trillo, 1993, Luzán 5, S.A. Ediciones, Madrid, or in other regular or similar publications of the Spanish Pharmacopoeia and in the United States.

The compounds described in the present invention, their isomers, salts, derivatives, prodrugs or pharmaceutically acceptable solvates, as well as the pharmaceutical compositions that contain them, can be used in the method of the present invention together or in combination with other additional drugs in order to provide a combination therapy. Said additional drugs may form part of the same pharmaceutical composition, or alternatively may be provided in the form of a separate composition for administration simultaneously or non-simultaneously with the pharmaceutical composition that comprises a compound of formula (I) or (II), or an isomer, salt, derivative, prodrug or pharmaceutically acceptable solvate of the same.

It is envisaged that the composition is a pharmaceutical composition. In a preferred embodiment, the pharmaceutical composition further comprises another active principle. The use of the compounds of the invention is compatible with protocols in which the compounds of the formula (I) or (II) or their mixtures are used by themselves or in combination with other treatments or any medical procedure.

In a preferred embodiment, the disease mediated by the enzyme phosphodiesterase 7 is an inflammatory or autoimmune disease selected from intestinal inflammatory disease, inflammatory articular pathologies, atopical dermatitis and other inflammatory dermatological pathologies, neuritis, encephalitis, encephalomielitis and inflammatory pathologies that affect the central nervous systems (multiple sclerosis) or the peripheral nervous system, myositis, vasculitis, systemic lupus erythematosus, asthma, chronic obstructive pulmonary disease, infectious diseases that involve inflammation, or combinations thereof.

In another preferred embodiment, the disease mediated by the enzyme phosphodiesterase 7 is a neurodegenerative or neurological disease selected from Alzheimer's disease, Parkinson's disease, amyotrophic lateral sclerosis, cerebral ischaemia, post-encephalitic Parkinsonism, dystonias, Tourette's syndrome, periodic limb movement disorder, restless leg syndrome, epilepsy, or combinations thereof.

In another preferred embodiment, the disease mediated by the enzyme phosphodiesterase 7 is a psychiatric disease selected from psychotic disorders, schizophrenia, depression, bipolar disorder, attention deficit disorder, or combinations thereof.

In the most preferred embodiment, the disease mediated by the enzyme phosphodiesterase 7 is a neurodegenerative disease, and still more preferably, said disease is Alzheimer's disease or Parkinson's disease.

In another aspect, the present invention also relates to a compound of formula (II):

where $R_4$, $R_5$ y $R_6$ are selected independently from hydrogen, substituted or unsubstituted $C_1$-$C_4$ alkyl or halogen, and $R_7$ is selected from substituted or unsubstituted $C_3$-$C_6$ cycloalkyl, substituted or unsubstituted $C_1$-$C_4$ alkyl or 3-pyridinyl, with the condition that when $R_7$ is methyl or 3-pyridinyl, $R_5$ or $R_6$ are not hydrogen,
or their isomers, salts, derivatives, prodrugs or pharmaceutically acceptable solvates.

In a preferred embodiment, $R_4$ is $C_1$-$C_4$ alkyl and, more preferably, methyl.

In another preferred embodiment, $R_4$ is halogen and, more preferably, chlorine.

In a preferred embodiment, $R_5$ is $C_1$-$C_4$ alkyl and, more preferably, methyl.

In another preferred embodiment, $R_5$ is halogen and, more preferably, is selected from fluorine or bromine.

In another preferred embodiment, $R_6$ is halogen and, more preferably, fluorine.

In another preferred embodiment, $R_7$ is $C_3$-$C_6$ cycloalkyl and, more preferably, is selected from cyclohexyl or cyclopropyl.

In another preferred embodiment, $R_7$ is $C_1$-$C_4$ alkyl and, more preferably, is selected from methyl or tert-butyl.

In another preferred embodiment, $R_7$ is 3-pyridinyl.

In another preferred embodiment, the compound of formula (II) is selected from:
2-Cyclohexylmethylthio-3-phenyl-4-oxo-3,4-dihydroquinazoline (comp. 1)
3-(2-Bromophenyl)-2-cyclohexylmethylthio-4-oxo-3,4-dihydroquinazoline (comp. 2)
3-Phenyl-2-neopentylthio-4-oxo-3,4-dihydroquinazoline (comp. 5)
3-(2,6-Difluorophenyl)-8-methyl-2-neopentylthio-4-oxo-3,4-dihydroquinazoline (comp. 6)
8-Chloro-3-phenyl-2-neopentylthio-4-oxo-3,4-dihydroquinazoline (comp. 11)
3-(2-Methylphenyl)-2-neopentylthio-4-oxo-3,4-dihydroquinazoline (comp. 13)
3-(2-Bromophenyl)-2-cyclopropylmethylthio-4-oxo-3,4-dihydroquinazoline (comp. 14)
2-Cyclopropylmethylthio-3-(2,6-difluorophenyl)-8-methyl-4-oxo-3,4-dihydroquinazoline (comp. 15)
2-Ethylthio-3-(2,6-difluorophenyl)-4-oxo-3,4-dihydroquinazoline (comp. 17)

8-Chloro-2-ethylthio-3-(2,6-difluorophenyl)-4-oxo-3,4-dihydroquinazoline (comp. 18)

2-Ethylthio-3-(4-fluorophenyl)-4-oxo-3,4-dihydroquinazoline (comp. 19)

8-Chloro-2-(3-pyridylmethylthio)-4-oxo-3,4-dihydroquinazoline (comp. 25)

3-(2-Methylphenyl)-2-(3-pyridylmethylthio)-4-oxo-3,4-dihydroquinazoline (comp. 26)

In the most preferred embodiment, the compound of formula (II) is 3-Phenyl-2-neopentylthio-4-oxo-3,4-dihydroquinazoline (comp. 5)

As mentioned previously, unless indicated otherwise, the compounds of the present invention also include compounds that differ only in the presence of one or more isotopically enriched atoms. For example, compounds that have said structure except for the substitution of a hydrogen atom with a deuterium or tritium atom, or the substitution of a carbon atom with a $^{13}C$- or $^{14}C$-enriched carbon atom or a $^{15}N$-enriched nitrogen atom.

In a final aspect, the present invention relates to a method for obtaining a compound of formula (II) that comprises the addition of an alkylating agent of formula $Z—CH_2R_7$ to a compound of formula (III):

where Z is a halide selected from fluorine, chloride, bromide or iodide, and $R_4$, $R_5$, and $R_6$ are defined as explained previously.

In the most preferred embodiment, Z is bromine and the addition is carried out in the presence of a carbonate.

As mentioned previously, the compounds of the present invention are specific and selective inhibitors of enzyme PDE7, unlike other compounds of similar structure described in the state of the art that are dual inhibitors of PDE7 and PDE4. The inhibition of PDE4 is linked to an increase in undesired adverse or secondary effects such as nausea, vomiting or general intestinal discomfort. Therefore, the compounds of the present invention (specific inhibitors of PDE7, but not of PDE4) offer an advantage in therapeutic use compared with the dual PDE7/PDE4 inhibitors available in the state of the art and mentioned previously.

The compounds of the present invention also have a greater ability to cross the blood-brain barrier compared with the compounds of similar structure and dual PDE7/PDE4 inhibitory activity known in the state of the art. This provides an additional advantage for the compounds when using them in therapeutic treatments for diseases related to the central nervous system, such as the neurodegenerative, neurological, psychiatric, inflammatory or autoimmune diseases mentioned previously.

The compounds of the present invention do not have any cardiotoxic potential, unlike other molecules of similar structure already known in the state of the art, which can stimulate the opening of the cardiac hERG channel. This means that these compounds have greater safety for use in the development of new treatments.

Throughout the description and the claims, the word "comprises" and its variants do not imply the exclusion of other technical features, additives, components or steps.

To allow a better understanding, the present invention is described in more detail below with reference to the attached drawings, which are presented by way of example, and with reference to illustrative and non-limitative examples.

FIG. 1 shows the plasma and brain concentration of compounds 5 (3-Phenyl-2-neopentylthio-4-oxo-3,4-dihydroquinazoline) and TC3.6 (3-Phenyl-2,4-dithioxo-1,2,3,4-tetrahydroquinazoline, a dual inhibitor of PDE7 and PDE4, described in patent application PCT WO2008/113881), after the intraperitoneal administration of both compounds in mice at a dosage of 10 mg/kg of mouse (A and B, respectively) (average of three animals per point ±standard error of the average). The rhomboid points and the graph that they describe refer to the measurement of the concentration of the analysed compound (compound 5 or TC3.6) in the brains of the treated mice. The square points and the graph that they describe refer to the measurement of the concentration of the analysed compound (compound 5 or TC3.6) in plasma. The ordinate axis (y) indicates the concentration of the analysed compound in ng of compound per g of brain or ng of compound per ml of plasma, depending on whether brain or plasma is analysed. The abscissa axis (x) indicates the time elapsed since the administration of the corresponding compound (post-administration time), in hours.

FIG. 2 shows the plasma and brain concentration of compounds 5 (3-Phenyl-2-neopentylthio-4-oxo-3,4-dihydroquinazoline) and TC3.6 (3-Phenyl-2,4-dithioxo-1,2,3,4-tetrahydroquinazoline, a dual inhibitor of PDE7 and PDE4, described in patent application PCT WO2008/113881), after the oral administration of both compounds in mice at a dosage of 10 mg/kg of mouse (A and B, respectively) (average of three animals per point ±standard error of the average). The rhomboid points and the graph that they describe refer to the measurement of the concentration of the analysed compound (compound 5 or TC3.6) in the brains of the treated mice. The square points and the graph that they describe refer to the measurement of the concentration of the analysed compound (compound 5 or TC3.6) in plasma. The ordinate axis (y) indicates the concentration of the analysed compound in ng of compound per g of brain or ng of compound per ml of plasma, depending on whether brain or plasma is analysed. The abscissa axis (x) indicates the time elapsed since the administration of the corresponding compound (post-administration time), in hours.

BRIEF DESCRIPTION OF DRAWINGS

EXAMPLES

Example 1

General Method for Synthesising the Compounds of the Invention

The starting point for obtaining the compounds of the present invention was the corresponding tetrahydroquinazoline of formula (III) (as described above), which can be synthesised by following the procedure described in the document by Redondo M. et al., "Neuroprotective efficacy of quinazoline type phosphodiesterase 7 inhibitors in cellular cultures and experimental stroke model", Eur. J. Med. Chem. 47 (2012) 175-185. To a solution of the corresponding tetrahydroquinazoline in 5 mL of acetonitrile was added the alkylating agent in the presence of carbonate (0.5 M). The reaction mixture was agitated at the temperature and for the time indicated below for each case. Finally, the solvent was eliminated by evaporation at reduced pressure. After carrying out chromatographic purification of the residue by using the eluents indicated in each case, the compounds of the present invention indicated in each case were obtained.

2-Cyclohexylmethylthio-3-phenyl-4-oxo-3,4-dihydroquinazoline (compound 1): Obtained according to the general method described previously.

Reagents: 3-Phenyl-4-oxo-2-thioxo-1,2,3,4-tetrahydroquinazoline (0.59 mmol, 0.150 g), cyclohexylmethyl bromide (0.70 mmol, 0.099 mL), $K_2CO_3$ (0.0045 g).

The reaction conditions were: 1 hour under microwave radiation at 150° C.

Purification was carried out by means of silica gel column chromatography (hexane/ethyl acetate, in a ratio of 6:1 by volume).

The yield obtained was: a white solid (96 mg, 47%). P.f.: 148.1-149.8° C. $^1$H-RMN (300 MHz, $CDCl_3$) δ: 8.23 (dd, 1H, J=7.9 Hz), 7.73 (td, 1H, J=8.2, 1.5 Hz), 7.61 (d, 1H, J=8.2 Hz), 7.50-7.52 (m, 3H), 7.36 (td, 1H, J=8.0, 1.2 Hz), 7.32-7.28 (m), 3.08 (d, 2H, J=6.7 Hz), 1.85-1.60 (m, 5H), 1.24-0.93 (m, 6H). $^{13}$C-RMN (75 MHz, $CDCl_3$) δ: 161.9, 157.9, 147.8, 136.1, 134.5, 129.8, 129.6, 129.2, 127.2, 126.2, 125.6, 119.8, 39.5, 37.2, 32.7, 26.2, 25.9, purity analysed by High Pressure Liquid Chromatography (HPLC) >99%. EM (m/z): 352 [M+H]$^+$. Elemental analysis ($C_{21}H_{22}N_2OS$): theoretical % C, 71.97; % H, 6.33; % N, 7.99; % S, 9.15. observed % C, 71.88; % H, 6.28; % N, 8.03; % S, 8.99.

3-(2-Bromophenyl)-2-cyclohexylmethylthio-4-oxo-3,4-dihydroquinazoline (compound 2): Obtained according to the general method described previously.

Reagents: 3-(2-Bromophenyl)-4-oxo-2-thioxo-1,2,3,4-tetrahydroquinazoline (0.30 mmol, 0.100 g), cyclohexylmethyl bromide (0.90 mmol, 0.125 mL), $K_2CO_3$ (0.0045 g).

The reaction conditions were: 12 hours at ambient temperature.

Purification was carried out by means of silica gel column chromatography (hexane/ethyl acetate, in a ratio of 6:1 by volume).

The yield obtained was: a white solid (100 mg, 77%). P.f. 129.5-132.0° C. $^1$H-RMN (400 MHz, DMSO) δ: 8.05 (dd, 1H, J=7.7 Hz), 7.85-7.79 (m, 2H), 7.64-7.54 (m, 3H), 7.50-7.43 (m, 2H), 3.16-2.97 (m, 2H), 1.74-1.52 (m, 6H), 1.14-0.89 (m, 5H). $^{13}$C-RMN (100 MHz, DMSO) δ: 160.6, 157.5, 147.9, 135.9, 135.7, 134.0, 132.6, 132.3, 129.7, 127.3, 126.7, 123.8, 119.8, 38.8, 37.5, 32.7, 32.6, 26.4, 26.1, purity analysed by HPLC 98%. EM (m/z): 429, 431 [M+H]$^+$.

3-Phenyl-2-neopentylthio-4-oxo-3,4-dihydroquinazoline (compound 5): Obtained according to the general method described previously.

Reagents: 3-Phenyl-4-oxo-2-thioxo-1,2,3,4-tetrahydroquinazoline (0.59 mmol, 0.150 g), neopentyl bromide (0.70 mmol, 0.092 mL), $K_2CO_3$ (0.0045 g).

The reaction conditions were: 1 hour under microwave radiation at 150° C.

Purification was carried out by means of silica gel column chromatography (hexane/ethyl acetate, in a ratio of 6:1 by volume).

The yield obtained was: a white solid (84 mg, 44%). P.f.: 161.0-162.1° C. $^1$H-RMN (300 MHz, $CDCl_3$) δ: 8.23 (dd, 1H, J=7.9, 1.5 Hz), 7.75-7.30 (m, 13H), 3.24 (s, 2H), 1.06 (s, 9H). $^{13}$C-RMN (75 MHz, $CDCl_3$) δ: 162.4, 158.3, 148.1, 136.6, 134.9, 129.7, 129.6, 129.2, 127.2, 126.1, 125.6, 46.2, 32.3, 29.3, purity analysed by HPLC >99%. EM (m/z): 325 [M+H]$^+$. Elemental analysis ($C_{19}H_{20}N_2OS$): theoretical % C, 70.34; % H, 6.21; % N, 8.63; % S, 9.88. observed % C, 70.12; % H, 6.50; % N, 8.66; % S, 9.69.

3-(2,6-Difluorophenyl)-8-methyl-2-neopentylthio-4-oxo-3,4-dihydroquinazoline (compound 6): Obtained according to the general method described previously.

Reagents: 3-(2,6-Difluorophenyl)-8-methyl-4-oxo-2-thioxo-1,2,3,4-tetrahydroquinazoline (0.32 mmol, 0.097 g), neopentyl bromide (0.64 mmol, 0.080 mL), $K_2CO_3$ (0.0045 g).

The reaction conditions were: 12 hours at ambient temperature.

Purification was carried out by means of silica gel column chromatography (hexane/ethyl acetate, in a ratio of 6:1 by volume).

The yield obtained was: a white solid (51 mg, 42%). P.f.: 152.3° C. $^1$H-RMN (400 MHz, DMSO) δ: 7.94 (dd, 1H, J=7.9, 0.8 Hz), 7.81-7.73 (m, 2H), 7.49-7.40 (m, 3H), 3.34 (s, 2H), 2.60 (s, 3H), 0.95 (s, 9H). $^{13}$C-RMN (100 MHz, DMSO) δ: 160.7, 158.8 (d, 2C, J=252.2 Hz), 156.0, 145.9, 136.9, 135.1, 134.1, 126.9, 125.1, 118.8, 113.5, 44.9, 32.6, 28.9, 17.6, purity analysed by HPLC >99%. EM (m/z): 375 [M+H]$^+$.

8-Chloro-3-phenyl-2-neopentylthio-4-oxo-3,4-dihydroquinazoline (compound 11): Obtained according to the general method described previously.

Reagents: 8-Chloro-3-phenyl-4-oxo-2-thioxo-1,2,3,4-tetrahydroquinazoline (0.173 mmol, 0.050 g), neopentyl bromide (0.312 mmol, 0.04 mL), $Cs_2CO_3$ (0.169 g).

The reaction conditions were: 2 hours under microwave radiation at 150° C.

Purification was carried out by means of centrifugal circular chromatography (hexane/ethyl acetate, in a ratio of 18:1 by volume).

The yield obtained was: a yellow solid (18.4 mg, 30%). P.f.: 128.0-130.1° C. $^1$H-RMN (400 MHz, $CDCl_3$) δ: 8.14 (dd, 1H, J=8.0, 1.5 Hz), 7.80 (dd, 1H, J=7.8, 1.5 Hz), 7.60-7.49 (m, 3H), 7.35-7.26 (m, 3H), 3.34 (s, 2H), 1.00 (s, 9H). $^{13}$C-RMN (100 MHz, $CDCl_3$) δ: 161.7, 159.6, 144.4, 136.1, 135.0, 130.9, 130.2, 130.0, 129.2, 126.2, 125.7, 121.5, 46.1, 32.4, 29.0, purity analysed by HPLC >99%. EM (m/z): 359 [M+H]$^+$. Elemental analysis ($C_{19}H_{19}ClN_2OS$): theoretical % C, 63.59; % H, 5.34; % N, 7.81; % S, 8.93. observed % C, 63.60; % H, 5.51; % N, 7.66; % S, 8.59.

3-(2-Methylphenyl)-2-neopentylthio-4-oxo-3,4-dihydroquinazoline (compound 13): Obtained according to the general method described previously.

Reagents: 3-(2-Methylphenyl)-4-oxo-2-thioxo-1,2,3,4-tetrahydroquinazoline (0.373 mmol, 0.100 g), neopentyl bromide (0.559 mmol, 0.07 mL), $Cs_2CO_3$ (0.364 g).

The reaction conditions were: 3 hours under microwave radiation at 150° C.

Purification was carried out by means of centrifugal circular chromatography (hexane/ethyl acetate, in a ratio of 10:1 by volume).

The yield obtained was: a yellow solid (55.0 mg, 44%). P.f.: 116.5-117.5° C. $^1$H-RMN (400 MHz, CDCl$_3$) δ: 8.25 (dd, 1H, J=8.0, 1.3 Hz), 7.77-7.6 (m, 1H), 7.63 (d, 1H, J=8.0 Hz), 7.50-7.33 (m, 4H), 7.20 (dd, 1H, J=7.2, 1.3 Hz), 3.32 (d, 1H, J=13.1 Hz), 3.17 (d, 1H, J=13.1 Hz), 2.17 (s, 2H), 0.98 (s, 9H). $^{13}$C-BMN (100 MHz, CDCl$_3$) δ: 161.6, 158.1, 148.0, 137.0, 135.3, 134.7, 131.5, 130.3, 129.3, 127.5, 126.2, 125.8, 119.9, 45.5, 32.2, 29.1, 17.6. Purity analysed by HPLC >99%. EM (m/z): 339 [M+H]$^+$. Elemental analysis (C$_{20}$H$_{22}$N$_2$OS): theoretical % C, 70.97; % H, 6.55; % N, 8.28; % S, 9.47. observed % C, 70.95; % H, 6.49; % N, 8.24; % S, 9.28.

3-(2-Bromophenyl)-2-cyclopropylmethylthio-4-oxo-3,4-dihydroquinazoline (compound 14): Obtained according to the general method described previously.

Reagents: 3-(2-Bromophenyl)-4-oxo-2-thioxo-1,2,3,4-tetrahydroquinazoline (0.42 mmol, 0.150 g), cyclopropylmethyl bromide (0.85 mmol, 0.083 mL), K$_2$CO$_3$ (0.0045 g).

The reaction conditions were: 12 hours at ambient temperature.

Purification was carried out by means of silica gel column chromatography (hexane/ethyl acetate, in a ratio of 6:1 by volume).

The yield obtained was: a white solid (161 mg, 98%). P.f.: 110.8-113.5° C. $^1$H-RMN (400 MHz, DMSO) δ: 8.06 (dd, 1H, J=7.9 Hz), 7.86-7.80 (m, 2H), 7.65-7.56 (m, 3H), 7.51-7.43 (m, 2H), 3.10 (d, 2H, J=7.4 Hz), 1.13-1.05 (m, 1H), 0.48 (dd, 2H, J=8.1 Hz), 0.25 (dd, 2H, J=6.7 Hz). $^{13}$C-RMN (100 MHz, DMSO) δ: 160.6, 157.6, 147.9, 136.9, 135.9, 135.7, 134.0, 132.3, 129.7, 127.3, 126.7, 123.8, 119.8, 117.3, 38.1, 10.5, 6.3, purity analysed by HPLC 98%. EM (m/z): 389 [M+Na]$^+$. Elemental analysis (C$_{18}$H$_{15}$BrN$_2$OS): theoretical % C, 56.86; % H, 4.27; % N, 6.98; % S, 7.99. observed % C, 56.48; % H, 3.89; % N, 7.21; % S, 8.05.

2-Cyclopropylmethylthio-3-(2,6-difluorophenyl)-8-methyl-4-oxo-3,4-dihydroquinazoline (compound 15): Obtained according to the general method described previously.

Reagents: 3-(2.6-Difluorophenyl)-8-methyl-4-oxo-2-thioxo-1,2,3,4-tetrahydroquinazoline (0.32 mmol, 0.097 g), cyclopropylmethyl bromide (0.96 mmol, 0.096 mL), K$_2$CO$_3$ (0.0045 g).

The reaction conditions were: 12 hours at ambient temperature.

Purification was carried out by means of silica gel column chromatography (hexane/ethyl acetate, in a ratio of 6:1 by volume).

The yield obtained was: a white solid (145 mg, 99%). P.f.: 143.6-146.3° C. $^1$H-RMN (400 MHz, DMSO) δ: 7.94 (d, 1H, J=7.9 Hz), 7.80-7.73 (m, 2H), 7.48-7.40 (m, 3H), 3.21 (d, 2H, J=7.3 Hz), 2.58 (s, 3H), 1.29-1.19 (m, 1H), 0.56-0.29 (m, 4H). $^{13}$C-RMN (100 MHz, DMSO) δ: 160.3, 158.8 (d, 2C, J=252.5 Hz), 156.2, 146.2, 136.8, 135.2, 134.0, 126.5, 125.0, 118.8, 113.6, 38.3, 17.6, 10.5, 6.4, purity analysed by HPLC >99%. EM (m/z): 359 [M+H]$^+$.

2-Ethylthio-3-phenyl-4-oxo-3,4-dihydroquinazoline (compound 16): Obtained according to the general method described previously.

Reagents: 3-Phenyl-4-oxo-2-thioxo-1,2,3,4-tetrahydroquinazoline (0.78 mmol, 0.200 g), diethyl sulphate (0.94 mmol, 0.122 mL), K$_2$CO$_3$ (0.3450 g).

The reaction conditions were: 1 hour under microwave radiation at 150° C.

Purification was carried out by means of silica gel column chromatography (hexane/ethyl acetate, in a ratio of 6:1 by volume).

The yield obtained was: a white solid (94 mg, 43%). P.f.: 117.5-119.6° C. $^1$H-RMN (300 MHz, CDCl$_3$) δ: 8.28 (dd, 1H, J=7.9, 1.5 Hz), 8.25 (m, 1H), 7.80-7.34 (m, 7H), 3.21 (d, 2H, J=7.4 Hz), 1.39 (t, J=7.4 Hz, 3H), $^{13}$C-RMN (75 MHz, CDCl$_3$) δ: 162.3, 157.8, 148.4, 136.5, 134.9, 130.3, 130.0, 129.6, 127.6, 126.6, 126.6, 27.4, 14.2, purity analysed by HPLC 99%. EM (m/z): 283 [M+H]$^+$. Elemental analysis (C$_{16}$H$_{14}$N$_2$OS): theoretical % C, 68.06; % H, 5.00; % N, 9.92; % S, 11.36. observed % C, 68.33; % H, 4.98; % N, 10.05; % S, 11.21.

2-Ethylthio-3-(2,6-difluorophenyl)-4-oxo-3,4-dihydroquinazoline (compound 17): Obtained according to the general method described previously.

Reagents: 3-(2,6-Difluorophenyl)-4-oxo-2-thioxo-1,2,3,4-tetrahydroquinazoline (0.28 mmol, 0.088 g), diethyl sulfate (0.86 mmol, 0.115 mL), K$_2$CO$_3$ (0.0045 g).

The reaction conditions were: 1 hour under microwave radiation at 150° C.

Purification was carried out by means of silica gel column chromatography (hexane/ethyl acetate, in a ratio of 6:1 by volume).

The yield obtained was: a white solid (53 mg, 58%). P.f.: 154.1-155.2° C. $^1$H-RMN (400 MHz, DMSO) δ: 8.10 (dd, 1H, J=7.9, 1.5 Hz), 7.89 (td, 1H, J=7.2, 1.5 Hz), 7.75 (m, 1H), 7.65 (dd, 1H, J=7.1, 1.5 Hz), 7.53 (td, 1H, J=7.2, 1.5 Hz), 7.44 (t, 2H, J=7.4 Hz), 3.18 (c, 2H, J=7.3 Hz), 1.29 (t, 3H, J=14.6 Hz). $^{13}$C-RMN (100 MHz, DMSO) δ: 160.4 (d, 2C, J=246.8 Hz), 160.1, 157.5, 147.8, 136.6, 134.1, 127.4, 127.1, 118.9, 113.6, 113.4, 26.6, 14.6, purity analysed by HPLC >99%. MS (ES, m/z): 319 [M+H]$^+$. Elemental analysis (C$_{16}$H$_{12}$F$_2$N$_2$OS): theoretical % C, 60.37; % H, 3.80; % N, 8.80; % S, 10.07. observed % C, 60.42; % H, 3.93; % N, 8.84; % S, 9.98.

8-Chloro-2-ethylthio-3-(2,6-difluorophenyl)-4-oxo-3,4-dihydroquinazoline (compound 18): Obtained according to the general method described previously.

Reagents: 8-Chloro-3-(2,6-difluorophenyl)-4-oxo-2-thioxo-1,2,3,4-tetrahydroquinazoline (0.45 mmol, 0.160 g), diethyl sulphate (1.35 mmol, 0.178 mL), K$_2$CO$_3$ (0.0045 g).

The reaction conditions were: 1 hour under microwave radiation at 150° C.

Purification was carried out by means of silica gel column chromatography (hexane/ethyl acetate, in a ratio of 6:1 by volume).

The yield obtained was: a white solid (52 mg, 33%). P.f.: 165.4-166.7° C. $^1$H-RMN (400 MHz, DMSO) δ: 8.05 (dd, 2H, J=7.8, 1.6 Hz), 7.76 (m, 1H), 7.47 (m, 3H), 3.23 (c, 2H, J=7.3 Hz), 1.34 (t, 3H, J=7.3 Hz). $^{13}$C-RMN (100 MHz, DMSO) δ: 163.1 (d, 2C, J=246.8 Hz), 161.5, 159.8, 144.4, 136.6, 132.5, 127.2, 125.7, 120.7, 116.1, 114.1, 113.9, 27.2, 14.7, purity analysed by HPLC 97%. MS (ES) m/z: 353 [M+H]$^+$. Elemental analysis (C$_{16}$H$_{11}$ClF$_2$N$_2$OS): theoretical % C, 54.47; % H, 3.14; % N, 7.94; % S, 9.09. observed % C, 54.19; % H, 2.89; % N, 8.06; % S, 8.79.

2-Ethylthio-3-(4-fluorophenyl)-4-oxo-3,4-dihydroquinazoline (compound 19): Obtained according to the general method described previously.

Reagents: 3-(4-Fluorophenyl)-4-oxo-2-thioxo-1,2,3,4-tetrahydroquinazoline (0.38 mmol, 0.104 g), diethyl sulphate (1.14 mmol, 0.151 mL), K$_2$CO$_3$ (0.0045 g).

The reaction conditions were: 1 hour under microwave radiation at 150° C.

Purification was carried out by means of silica gel column chromatography (hexane/ethyl acetate, in a ratio of 6:1 by volume).

The yield obtained was: a white solid (70 mg, 61%). P.f.: 130.7-131.8° C. $^1$H-RMN (400 MHz, DMSO) δ: 8.04 (dd, 1H, J=7.9, 1.2 Hz), 7.80 (td, 2H, J=8.3, 1.5 Hz), 7.60-7.36 (m, 5H), 3.10 (c, 2H, J=14.7, 7.3 Hz), 1.36 (t, 3H, J=7.3 Hz). $^{13}$C-RMN (100 MHz, DMSO) δ: 163.1 (d, 2C, J=246.8 Hz), 161.5, 158.0, 148.0, 135.5, 132.5, 127.2, 125.7, 126.5, 120.2, 117.1, 116.9, 26.9, 14.5, purity analysed by HPLC >99%. MS (ES) m/z: 301 [M+H]$^+$. Elemental analysis ($C_{16}H_{13}FN_2OS$): theoretical % C, 63.98; % H, 4.36; % N, 9.33; % S, 10.68. observed % C, 63.75; % H, 4.26; % N, 9.29; % S, 10.47.

2-Benzylthio-3-phenyl-4-oxo-3,4-dihydroquinazoline (compound 21): Obtained according to the general method described previously.

Reagents: 3-Phenyl-4-oxo-2-thioxo-1,2,3,4-tetrahydroquinazoline (0.59 mmol, 0.150 g), benzyl bromide (0.71 mmol, 0.084 mL), $K_2CO_3$ (0.3450 g).

The reaction conditions were: 1 hour under microwave radiation at 150° C.

Purification was carried out by means of silica gel column chromatography (hexane/ethyl acetate, in a ratio of 8:1 by volume).

The yield obtained was: a white solid (61 mg, 30%). P.f.: 175.0-176.0° C. $^1$H-RMN (300 MHz, CDCl$_3$) δ: 8.28 (dd, 1H, J=7.9, 1.5 Hz), 7.80 (td, 1H, J=8.2, 1.5 Hz), 7.72 (d, 1H, J=8.2 Hz), 7.57-7.33 (m, 11H), 4.42 (s, 2H). $^{13}$C-RMN (75 MHz, CDCl$_3$) δ: 162.2, 157.5, 148.2, 136.8, 136.2, 135.0, 130.3, 130.1, 129.8, 129.6, 128.9, 127.9, 127.7, 126.6, 126.3, 120.4, 37.5, purity analysed by HPLC 99%. EM (m/z): 345 [M+H]$^+$. Elemental analysis ($C_{21}H_{16}N_2OS$): theoretical % C, 72.70; % H, 4.27; % N, 8.48; % S, 9.70. observed % C, 73.00; % H, 4.27; % N, 8.26; % S, 9.58.

3-Phenyl-2-(2-pyridylmethylthio)-4-oxo-3,4-dihydroquinazoline (compound 23): Obtained according to the general method described previously.

Reagents: 3-Phenyl-4-oxo-2-thioxo-1,2,3,4-tetrahydroquinazoline (0.80 mmol, 0.200 g), 2-bromomethylpyridine hydrobromide (1.2 mmol, 303.5 mg), $Cs_2CO_3$ (0.8145 g).

The reaction conditions were: 3 hours under microwave radiation at 150° C.

Purification was carried out by means of silica gel column chromatography (hexane/ethyl acetate, in a ratio of 4:1 by volume).

The yield obtained was: a white solid (157 mg, 57%). P.f.: 173.0-174.0° C. $^1$H-RMN (400 MHz, CDCl$_3$) δ: 8.45 (ddd, 1H, J=4.8, 1.9, 1.0 Hz), 8.06 (dd, 1H, J=8.0, 1.5 Hz), 7.83 (ddd, 1H, J=8.6, 7.2, 1.6 Hz), 7.72 (td, 1H, J=7.6, 1.8 Hz), 7.65 (dd, 1H, J=7.6, 1.1 Hz), 7.60-7.49 (m, 3H), 7.43-7.39 (m, 4H), 7.24 (ddd, 1H, J=7.6, 4.8, 1.1 Hz), 4.50 (s, 2H). $^{13}$C-RMN (100 MHz, CDCl$_3$) δ: 162.0, 156.8, 156.6, 148.3, 147.9, 135.8, 135.6, 135.0, 130.3, 130.0, 129.4, 127.5, 126.4, 126.2, 124.5, 122.9, 120.2, 38.8, purity analysed by HPLC 99%. EM (m/z): 346 [M+H]$^+$. Elemental analysis ($C_{20}H_{15}N_3OS$): theoretical % C, 69.54; % H, 4.38; % N, 12.17; % S, 9.28. observed % C, 69.81; % H, 4.65; % N, 12.32; % S, 9.00.

3-Phenyl-2-(3-pyridylmethylthio)-4-oxo-3,4-dihydroquinazoline (compound 24): Obtained according to the general method described previously.

Reagents: 3-Phenyl-4-oxo-2-thioxo-1,2,3,4-tetrahydroquinazoline (0.80 mmol, 0.200 g), 3-bromomethylpyridine hydrobromide (1.2 mmol, 303.5 mg), $Cs_2CO_3$ (0.8145 g).

The reaction conditions were: 2 hours under microwave radiation at 150° C.

Purification was carried out by means of silica gel column chromatography (hexane/ethyl acetate, in a ratio of 4:1 by volume).

The yield obtained was: a white solid (127 mg, 46%). P.f.: 154.0-155.0° C. $^1$H RMN (400 MHz, CDCl$_3$) δ: 8.71 (d, 1H, J=2.5 Hz), 8.49 (d, 1H, J=4.4 Hz), 8.24 (d, 1H, J=8.0 Hz), 7.80-7.77 (m, 1H), 7.75 (d, 1H, J=6.9 Hz), 7.67 (d, 1H, J=8.2 Hz), 7.57-7.50 (m, 3H), 7.42 (t, 1H, J=7.5 Hz), 7.33-7.25 (m, 3H), 4.38 (s, 2H). $^{13}$C RMN (100 MHz, CDCl$_3$) δ: 161.9, 156.3, 150.0, 148.0, 147.8, 135.8, 135.1, 133.8, 130.4, 130.0, 129.4, 127.6, 126.4, 126.2, 123.8, 123.7, 120.2, 34.0, purity analysed by HPLC 98%. EM (m/z): 346 [M+H]$^+$. Elemental analysis ($C_{20}H_{15}N_3OS$): theoretical % C, 69.54; % H, 4.38; % N, 12.17; % S, 9.28. observed % C, 69.75; % H, 4.61; % N, 12.02; % S, 9.05.

8-Chloro-2-(3-pyridylmethylthio)-4-oxo-3,4-dihydroquinazoline (compound 25): Obtained according to the general method described previously.

Reagents: 8-Chloro-4-oxo-2-thioxo-1,2,3,4-tetrahydroquinazoline (0.173 mmol, 0.050 g), 3-pyridylmethyl bromide (0.311 mmol, 0.788 g), $Cs_2CO_3$ (0.203 g).

The reaction conditions were: 2 hours 30 minutes under microwave radiation at 150° C.

Purification was carried out by means of centrifugal circular chromatography (hexane/ethyl acetate, in a ratio of 5:1 by volume).

The yield obtained was: a white solid (14.3 mg, 22%). P.f.: 191.5-192.5° C. $^1$H-RMN (400 MHz, CDCl$_3$) δ: 8.76 (d, 1H, J=2.4 Hz), 8.50 (s, 1H), 8.16 (dd, 1H, J=8.0, 1.5 Hz), 7.94 (d, 1H, J=7.9 Hz), 7.84 (dd, 1H, J=7.9, 1.5 Hz), 7.59-7.51 (m, 3H), 7.37-7.27 (m, 4H), 4.48 (s, 2H). $^{13}$C-RMN (100 MHz, CDCl$_3$) δ: 161.4, 158.0, 149.9, 148.0, 144.3, 137.9, 135.5, 135.3, 133.9, 131.0, 130.6, 130.1, 129.2, 126.3, 123.9, 121.7, 34.0, purity analysed by HPLC 98%. MS (ES) m/z: 360 [M+H]$^+$. Elemental analysis: ($C_{20}H_{14}ClN_3OS$): theoretical % C, 63.24; % H, 3.71; % N, 11.06; % S, 8.44. observed % C, 62.40; % H, 3.99; % N, 11.65; % S, 8.01.

3-(2-Methylphenyl)-2-(3-pyridylmethylthio)-4-oxo-3,4-dihydroquinazoline (compound 26): Obtained according to the general method described previously.

Reagents: 3-(2-Methylphenyl)-4-oxo-2-thioxo-1,2,3,4-tetrahydroquinazoline (0.3730 mmol, 0.100 g), 3-pyridylmethyl bromide (0.559 mmol, 0.141 g), $Cs_2CO_3$ (0.364 g).

The reaction conditions were: 3 hours under microwave radiation at 150° C.

Purification was carried out by means of centrifugal circular chromatography (hexane/ethyl acetate, in a ratio of 6:1 by volume).

The yield obtained was: a white solid (16.3 mg, 12%). P.f.: 150.0-151.8° C. $^1$H-RMN (400 MHz, CDCl$_3$) δ 8.71 (s, 1H), 8.48 (s, 1H), 8.26 (dd, 1H, J=8.2, 1.3 Hz), 7.81-7.75 (m, 2H), 7.72 (d, 1H, J=7.6 Hz), 7.48-7.40 (m, 2H), 7.40-7.31 (m, 2H), 7.28-7.26 (m, 1H), 7.18 (dd, J=7.6, 1.3 Hz, 1H), 4.40 (d, 1H, J=14.1 Hz), 4.35 (d, 1H, J=14.1 Hz), 2.10 (s, 3H). $^{13}$C-RMN (100 MHz, CDCl$_3$) δ: 161.3, 156.3, 150.1, 148.1, 147.9, 137.5, 137.0, 135.0, 134.8, 133.8, 131.6, 130.6, 129.3, 127.6, 126.4, 126.3, 123.8, 120.0, 33.7, 17.6, purity analysed by HPLC >99%. MS (ES) m/z: 360 [M+H]$^+$. Elemental analysis: ($C_{21}H_{17}N_3OS$): theoretical % C, 70.17; % H, 4.77; % N, 11.63; % S, 8.92. observed % C, 69.87; % H, 5.02; % N, 11.82; % S, 8.87.

3-Phenyl-2-(4-pyridylmethylthio)-4-oxo-3,4-dihydroquinazoline (compound 27): Obtained according to the general method described previously.

Reagents: 3-Phenyl-4-oxo-2-thioxo-1,2,3,4-tetrahydroquinazoline (0.80 mmol, 0.200 g), 4-bromomethylpyridine hydrobromide (1.2 mmol, 303.5 mg), $Cs_2CO_3$ (0.8145 g).

The reaction conditions were: 3 hours under microwave radiation at 150° C.

Purification was carried out by means of silica gel column chromatography (hexane/ethyl acetate, in a ratio of 10:1 by volume).

The yield obtained was: a white solid (130 mg, 47%). P.f.: 178.0-179.0° C. $^1$H-RMN (400 MHz, $CDCl_3$) δ: 8.53 (d, 2H, J=6.1 Hz), 8.24 (dd, 1H, J=7.9, 1.5 Hz), 7.81-7.71 (m, 1H), 7.65-7.58 (m, 1H), 7.57-7.39 (m, 4H), 7.38 (d, 2H, J=6.1 Hz), 7.33-7.28 (m, 2H), 4.37 (s, 2H). $^{13}$C-RMN (100 MHz, $CDCl_3$) δ: 161.6, 155.8, 149.5, 147.5, 147.2, 135.5, 134.8, 130.2, 129.8, 129.1, 127.4, 126.2, 126.1, 124.4, 119.9, 35.2, purity analysed by HPLC 99%. EM (m/z): 346 $[M+H]^+$. Elemental analysis ($C_{20}H_{15}N_3OS$): theoretical % C, 69.54; % H, 4.38; % N, 12.17; % S, 9.28. observed % C, 69.38; % H, 4.45; % N, 12.06; % S, 9.30.

3-Phenyl-2-(2-naphthylmethylthio)-4-oxo-3,4-dihydroquinazoline (compound 28): Obtained according to the general method described previously.

Reagents: 3-Phenyl-4-oxo-2-thioxo-1,2,3,4-tetrahydroquinazoline (0.40 mmol, 0.100 g), 2-naphthylmethyl bromide (0.60 mmol, 132.7 mg), $Cs_2CO_3$ (0.8145 g).

The reaction conditions were: 3 hours under microwave radiation at 150° C.

Purification was carried out by means of silica gel column chromatography (hexane/ethyl acetate, in a ratio of 10:1 by volume).

The yield obtained was: a white solid (30 mg, 19%). P.f.: 223.0-224.0° C. $^1$H-RMN (400 MHz, DMSO) δ: 7.99 (dd, 1H, J=8.0, 1.5 Hz), 7.94-7.90 (m, 1H), 7.82-7.68 (m, 5H), 7.50-7.32 (m, 9H), 4.56 (s, 2H). $^{13}$C-RMN (100 MHz, DMSO) δ: 161.4, 157.5, 147.9, 136.5, 135.7, 135.0, 133.4, 132.8, 130.5, 130.2, 130.1, 128.8, 128.7, 128.3, 128.2, 128.1, 127.3, 127.0, 126.8, 126.7, 120.3, 39.5, purity analysed by HPLC 98%. EM (m/z): 395 $[M+H]^+$. Elemental analysis ($C_{25}H_{18}N_2OS$): theoretical % C, 76.12; % H, 4.60; % N, 7.10; % S, 8.13. observed % C, 75.86; % H, 5.04; % N, 7.25; % S, 7.96.

Example 2

Measurement of the PDE7 Inhibition of the Compounds of the Invention

Measurement of PDE7 inhibition was carried out using a commercial phosphodiesterase activity measurement kit.

Some of the compounds of the present invention (including those synthesised in Example 1) were evaluated. For this purpose, said compounds were incubated (in a range of concentrations from 0.1 nM to 100 μM) in the presence of 0.02 U/well of PDE7A1 and 0.05 μCi of [$^3$H] cAMP, for 20 minutes at 30° C. in the assay buffer supplied with the kit (total volume per well=100 μL). Once this time had elapsed, 50 μL of a 20 mg/mL suspension of SPA glass silicate microspheres were added and kept in agitation at ambient temperature for 60 minutes. After allowing the plate to rest for 20 minutes, the radioactivity was tested in a scintillation detector. All the assays included two points in the absence of PDE7A1 (blank/negative control) and two points with PDE7A1 in the absence of inhibitors (positive control).

Analysis of the data: All the compounds were initially evaluated at a concentration of 10 μM and the percentage inhibition of PDE7A1 was calculated according to the following formula:

% inhibition=((cpm control−cpm sample)×100)/(cpm control−cpm blank)

For those compounds with % inhibition values above 45%, their inhibitory power ($IC_{50}$) was calculated by constructing a concentration-response curve, following the protocol explained previously (concentration of analysed compound from 0.1 nM to 100 μM). The data were adjusted with a software program using non-linear adjustment.

TABLE 1

PDE inhibition data of the compounds of the present invention.

| Compound | PDE7A $IC_{50}$ (μM) | PDE4D3 | PDE4B2 |
|---|---|---|---|
| 1 | 0.20 | 49% @10 μM | 18% @10 μM |
| 2 | 2.11 | | |
| 5 | 0.10 | 37% @10 μM | 29% @10 μM |
| 6 | 8.67 | | |
| 11 | 1.2 | | |
| 13 | 1.85 | | |
| 14 | 9.44 | | |
| 15 | 4.56 | | |
| 16 | 6.90 | | |
| 17 | 6.99 | | |
| 18 | 2.44 | | |
| 21 | 0.60 | 38% @10 μM | 28% @10 μM |
| 23 | 0.80 | | |
| 24 | 0.70 | | |
| 25 | 0.54 | | |
| 26 | 0.12 | | |
| 27 | 2.6 | | |
| 28 | 0.09 | | |

Example 3

Assay of Permeability in the Central Nervous System (CNS), Using the Parallel Artificial Membrane Permeability Assay (PAMPA), of the Compounds of the Present Invention The prediction of the permeability of the various compounds in the central nervous system (CNS), i.e. their passage across the blood-brain barrier, was determined using the parallel artificial membrane permeability assay (PAMPA) (Di, L. et al., "High throughput artificial membrane permeability assay for blood-brain barrier", Eur. J. Med. Chem., 2003, 38 (3), 223-232). PDVF membrane filters were used for filtering the samples (diameter 30 mm, pore size 0.45 μm).

Ten reference compounds were selected whose passage across the blood-brain barrier is known and in the public domain, in order to validate the experiment. Different quantities of these compounds were taken, namely: 3-5 mg of caffeine, enoxacin, hydrocortisone, desipramine, ofloxacin, piroxicam and testosterone, 12 mg of promazine, and 25 mg of verapamil and atenolol, which were dissolved in ethanol (1000 μL). 100 μL of these solutions were taken, and 1400 μL of ethanol and 3500 μL of PBS (pH=7.4) were added in order to achieve a final ethanol concentration of 30% in the solution. The solutions were filtered. Afterwards, 180 μL of a solution of PBS/ethanol (70/30) were added to each well of the acceptor plate. The donor plate was impregnated with 4 μL of a solution of porcine brain lipid dissolved in dodecane (20 mg mL-1).

After 5 minutes, 180 μL of solution of each compound were added to this plate.

For the compounds to be evaluated for their penetration in the central nervous system (namely compounds 13, 14, 15, 16, 17, 23, 24, 25, 26 and 27), 1-2 mg of the compound were taken and dissolved in 1500 µL of ethanol and 3500 µL of PBS (pH=7.4), they were filtered and added to the 96-well donor plate.

The donor plate was then placed on the acceptor plate, forming a kind of sandwich, and left to incubate for 2 h and 30 min at 25° C. The compounds passed by passive transport from the donor plate, through the porcine brain lipid, to the acceptor plate. After 2 h and 30 min, the donor plate was carefully removed.

The concentration and absorbance, both of the commercial compounds and of the compounds of the present invention that were evaluated in the acceptor and donor plates, were determined using a UV absorbance reader. Each sample was analysed at different wavelengths (between 3 and 5 absorbance minima and maxima were chosen for each compound at wavelength valves of between 220 nm and 450 nm), in 3 wells and in a minimum of 2 independent experiments. The results are the average of the averages [±standard deviation] of the different experiments performed. The measurements were carried out on the acceptor plate.

In relation to the ten reference commercial compounds used in each experiment in order to validate the method, a good correlation was found between the experimental permeability (Pe) values and those described in the available bibliography (bibliographic permeability, Pb), Pe=(1.1512× Pb)−0.8973 ($R^2$=0.977). Based on this equation and following the model described in the literature (Crivori, P.; Cruciani, G.; Testa, B. "Predicting Blood-Brain Barrier Permeation from Molecular Three-Dimensional Structure", J. Med. Chem., 2000, 43, 2204-2216) for predicting the permeability of the blood-brain barrier, the compounds can be classified as permeable to the central nervous system (CNS) when they have a permeability $>3.71 \times 10^{-6}$ cm s$^{-1}$, and are classified as non-permeable to the CNS when they have a permeability of less than $1.40 \times 10^{-6}$ cm s$^{-1}$ (between these two values there is an area of uncertainty). The results are given in Table 2, where it can be seen that the majority of the assayed compounds are classified as capable of penetrating the blood-brain barrier.

TABLE 2

Permeability data (bibliographic and experimental) of the commercial or bibliographic compounds and experimental permeability data for the assayed compounds of the present invention.

| Compound | Pb ($10^{-6}$ cm s$^{-1}$) | Pe ($10^{-6}$ cm s$^{-1}$) | Permeability prediction |
|---|---|---|---|
| Atenolol | 0.8 | 0.2 ± 0.1 | |
| Caffeine | 1.3 | 0.8 ± 0.1 | |
| Desipramine | 12 | 8.0 ± 1.0 | |
| Enoxacin | 0.9 | 0.7 ± 0.2 | |
| Hydrocortisone | 1.9 | 0.3 ± 0.3 | |
| Ofloxacin | 0.8 | 0.2 ± 0.1 | |
| Piroxicam | 2.5 | 0.2 ± 0.1 | |
| Promazine | 8.8 | 8.5 ± 0.1 | |
| Testosterone | 17 | 17.2 ± 0.6 | |
| Verapamil | 16 | 14.7 ± 1.1 | |
| 16 | | 7.9 ± 1.2 | SNC+ |
| 17 | | 4.8 ± 0.6 | SNC+ |
| 14 | | 1.9 ± 0.3 | SNC+/− |
| 15 | | 1.3 ± 0.9 | SNC+/− |
| 23 | | 12.4 ± 2.2 | SNC+ |
| 24 | | 18.6 ± 1.7 | SNC+ |
| 27 | | 15.9 ± 1.3 | SNC+ |
| 26 | | 20.1 ± 0.1 | SNC+ |
| 25 | | 12.1 ± 3.9 | SNC+ |
| 13 | | 3.9 ± 0.7 | SNC+ |

Example 4

Study of Toxicity on the Cardiac hERG Channel

The hERG potassium channel contributes in the final phase of the action potential, bringing the cell to its resting state. If a drug suppresses the activity of the channel, it can produce a prolongation of the action of the channel, known as "long QT syndrome", resulting in a fatal ventricular arrhythmia.

To characterise the behaviour of the hERG potassium channel in the presence of the compounds of the present invention, use was made of an assay based on a fluorescent probe (FluxOR®, Life Technologies) with high affinity for thallium, an indicator of the activity of the potassium ion channel. When the potassium channels open in response to a stimulus, the influx of thallium from the external environment is detected by the probe. The fluorescent signal is therefore proportional to the number of open potassium channels in the cell. The FluxOR® is added in ester form without fluorescent emission capacity, thus preventing the emission of fluorescence outside the cell. When it enters the cell, the cytosol esterases activate the FluxOR®, so that it is capable of binding the thallium that passes into the cytoplasm through the hERG channel and of emitting fluorescence.

This example shows the results obtained for compound 5 of the present invention (3-Phenyl-2-neopentylthio-4-oxo-3,4-dihydroquinazoline), synthesised as indicated in Example 1, and the PDE7 and PDE4 dual inhibitor compound TC3.6 (3-Phenyl-2,4-dithioxo-1,2,3,4-tetrahydroquinazoline).

Black plates containing 96 wells treated with poly-D-lysine were seeded with HEK293 cells (deposit number ATCC CRL-1573) modified to stably express the hERG channel. After 24 hours, the plates were washed with assay buffer (NaCl 165 mM, KCl 4.5 mM, $CaCl_2$ 2 mM, $MgCl_2$ 1 mM, Hepes 10 mM and glucose 10 mM, pH 7.4), and 20 µL of FluxOR™ dissolved in assay buffer were added. After one hour of incubation of the fluorochrome with the cells at ambient temperature, the plates were washed with 50 µL of assay buffer. Subsequently, 20 µL of the compounds to be studied were added at a dilution of 1:200 (2 µL of compound/400 µL of assay buffer), in triplicate, on 12-point curves (1:2 dilutions of the compound in DMSO). The highest assayed concentration was 150 µM (initial concentration of the analysed compounds). After 30 minutes of incubation, the plates were read in a FLIPR TETRA®, which added 5 µL of stimulus buffer ($Tl_2SO_4$+$K_2SO_4$). The fluorescence reading was carried out for 120 seconds, allowing analysis of the kinetics of the channel. 1 µM of astemizol (which has an $IC_{50}$ of approximately 2.6 µM), bepridil ($IC_{50}$ of 1.4 µM), haloperidol ($IC_{50}$ of 1.16 µM) and terfenadine ($IC_{50}$ of 1.2 µM) were used as positive controls, while DMSO at 0.5% was used as a negative control.

Compound 5 showed very low activity, with an $IC_{50}$ of over µM (>30 µM). Compound TC3.6, on the other hand, stimulated the opening of the potassium channel, with an $IC_{50}$ (concentration required to produce 50% of the response) of 5.19 µM. From these data, it is deduced that compound 5 did not have any cardiotoxic potential.

Example 5

Pharmacokinetic Studies in Mice: Exposure in Plasma and Brain

This example shows the results of the pharmacokinetic studies carried out in mice for compound 5 of the present invention (3-Phenyl-2-neopentylthio-4-oxo-3,4-dihydroquinazoline), synthesised as indicated in Example 1, in comparison with the PDE7 and PDE4 dual inhibitor compound TC3.6 (3-Phenyl-2,4-dithioxo-1,2,3,4-tetrahydroquinazoline). In this case it was found that compound 5 can be quantified in plasma and brain (and is therefore capable of crossing the blood-brain barrier) at levels that prove its biological activity.

In a first step, the study was carried out by means of intraperitoneal administration of the compounds to be studied (compound 5 and TC3.6). For this study, healthy C57BL/6 mice were used (8-12 weeks old, with a weight of between 20-35 g), which were kept at 22±3° C. and a humidity of 40-70%, with water and food ad libitum in 12-hour cycles of light and dark. The study was carried out in accordance with the guidelines and with the approval of the Institutional Animal Ethics Committee (IAEC). 15 mice were injected intraperitoneally with a solution of the compound to be studied (2% v/v DMSO in water: Tocrisolve® (95:5)) at a dosage of 10 mg/kg. The administration volume was 10 mL/kg. Blood samples (of approximately 120 µL) were taken from the retro-orbital plexus of 3 mice for each point studied (0, 0.25, 0.5, 1, and 2 h after injection of the dose), and these were placed in microcentrifuge tubes containing 10 µL of $K_2$EDTA 20% w/v as anticoagulant. The plasma was obtained after centrifugation of the blood at 4000 rpm for 10 min at 4° C., and then stored at −70° C. until its analysis.

After the blood extraction, the mice of each group were sacrificed by asphyxia with $CO_2$, in order to obtain the brain. The brains were washed in a cold solution, dried in filter paper, weighed and placed in polypropylene tubes. The brains were homogenised with a buffered solution of phosphate pH 7.4, so that the total volume of the homogenate was three times the weight of the brain. The samples were stored at −70° C. until their analysis.

The extraction procedure for the plasma/brain homogenate or plasma calibration standard/doped brain samples was the same: 100 µL of the internal standard (imipramine, 500 ng/mL) were added, prepared in acetonitrile, to 25 µL of sample (plasma/brain) or doped calibration standard, and agitated with a vortex agitator for 5 minutes. As a blank (negative control), only acetonitrile was added. The samples were centrifugated for 10 min at 15000 rpm (20600 g) at 4° C. 100 µL of each supernatant were transferred to 96-well plates for its analysis by liquid chromatography-tandem mass spectrometry (LC-MS/MS). The calibration standards were prepared by doping 10 µL of analyte (compound to be studied, 1 mg/mL) in 190 µL of virgin plasma/brain homogenate (and subsequent serial dilutions).

The pharmacokinetic study was performed based on the time-concentration data obtained for the plasma and brain, by means of non-compartmental analysis using version 5.2 of WinNonlin®. The areas under the concentration-time curve (AUClast and AUCinf) were calculated using the linear trapezoidal rule.

In a second step, it was tested whether compound 5 of the present invention (3-Phenyl-2-neopentylthio-4-oxo-3,4-dihydroquinazoline) synthesised as indicated in Example 1 and the dual PDE7 and PDE4 inhibitor compound TC3.6 (3-Phenyl-2,4-dithioxo-1,2,3,4-tetrahydroquinazoline) could be administered via the oral route in such a way that they could be quantified in plasma and brain (and therefore to see whether they were capable of crossing the blood-brain barrier) at levels that would prove their biological activity.

For this purpose, a pharmacokinetic study similar to that described for the intraperitoneal administration was performed. The only difference lay in the administration of the compounds, which was via the oral route, in a suspension consisting of Tween 80 0.1% v/v and sodium carboxymethyl cellulose (NaCMC) 0.5% w/v in water. The compounds were administered at a dosage of 10 mg/kg, by gastric intubation using a 22-gauge oral feeding needle. The administration volume was 10 mL/kg.

As can be seen in Table 3, after both intraperitoneal and oral administration, the concentration of compound 5 in brain was higher than that of TC3.6, indicating that compound 5 was better at crossing the blood-brain barrier (brain/plasma exposure ratio of >1 for compound 5, compared with <1 for compound TC3.6—see Table 3). This provides an additional advantage when using the compounds of the present invention in treatments for diseases related to the central nervous system, such as the neurodegenerative, inflammatory or autoimmune diseases mentioned previously.

The clearest differences between the two compounds were observed after oral administration, where, having administered the same dose, the concentration of compound 5 was higher than that of TC3.6 in both plasma and brain. The concentration of compound 5 in plasma and brain was above its $IC_{50}$ for PDE7 (13.8× and 16.4× respectively—see Table 4), supporting its biological activity, whereas that of TC3.6 was found below its $IC_{50}$ for PDE7 (0.83× and 0.36× respectively—see Table 4). These data indicate a greater efficacy of the compounds of the present invention for use in the development of drugs.

Figure 1A:
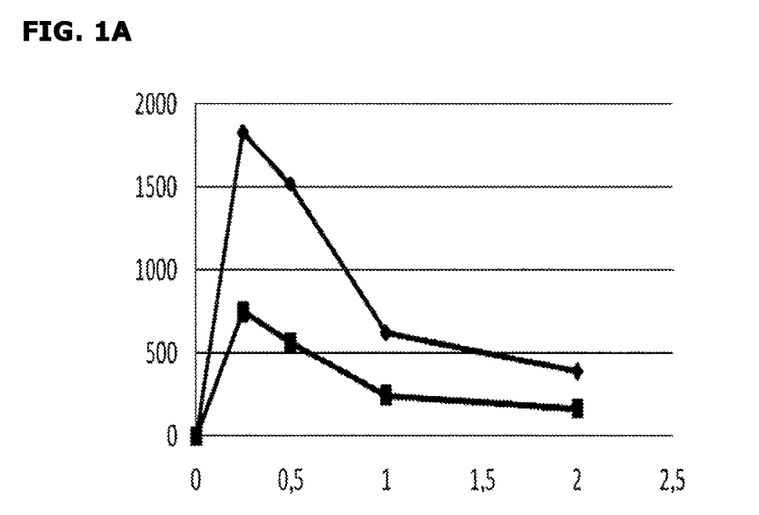
FIG. 1A shows the elimination of compound 5 in plasma wherein 2 hours after intraperitoneal or oral administration there were still considerable levels of this compound.
Figure 1B:
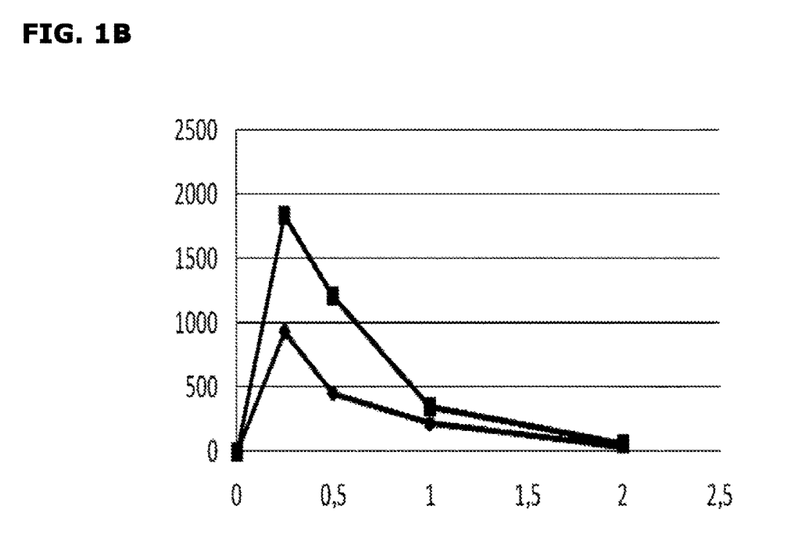
FIG. 1B shows the elimination of compound TC3.6 in plasma wherein 2 hours after administration the compound had been eliminated regardless of administration.
Figure 2A:
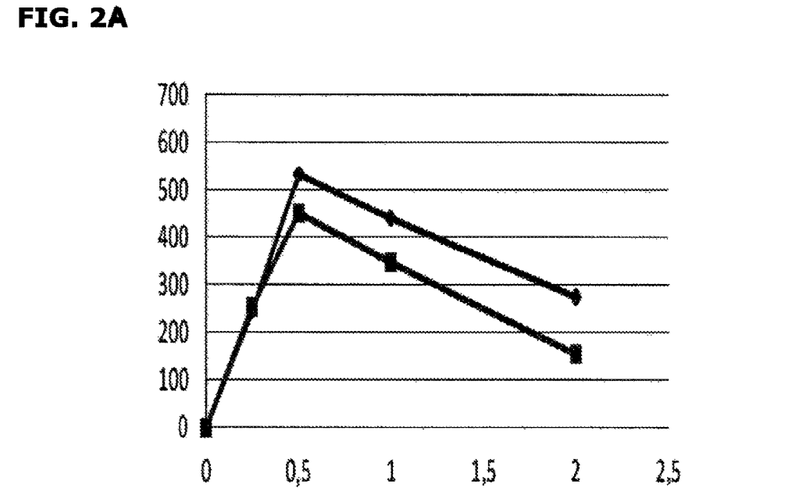
FIG. 2A shows the elimination of compound 5 in brain wherein 2 hours after intraperitoneal or oral administration there were still considerable levels of this compound.
Figure 2B:
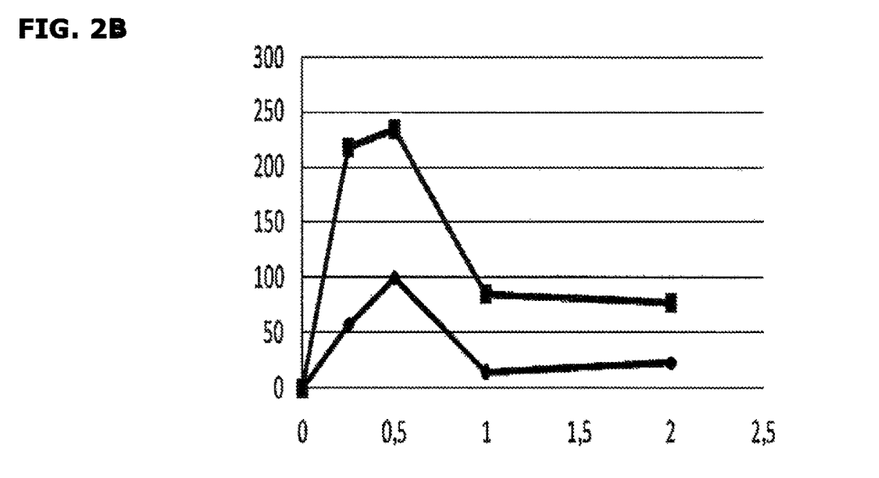
FIG. 2B shows the elimination of compound TC3.6 in brain wherein 2 hours after administration the compound had been eliminated regardless of administration.

As can be seen in FIGS. 1 and 2, the elimination of compound 5 in plasma and brain was slower, and 2 hours after intraperitoneal or oral administration there were still considerable levels of this compound in plasma and brain (see FIGS. 1A and 2A). In contrast, compound TC3.6 had been almost eliminated after two hours, regardless of the route of administration used (see FIGS. 1B and 2B). These data demonstrated the potential of the compounds of the present invention to be more effective at lower doses and, therefore, to avoid possible toxic effects by increasing the therapeutic effect.

The comparison of results relating to compound 5 and compound TC3.6 is summarised below in Tables 3 and 4.

TABLE 3

Comparison of the inhibitory activity of PDE7 in vitro and of concentration in plasma and brain after intraperitoneal and oral administration in mice of compound 5 and compound TC3.6.

| Comp. | PDE inhibitory activity PDE7A $CI_{50}$ (µM) | Intraperitoneal administration (Tmax 0.25 h) | | | Oral administration (Tmax 0.5 h) | | |
|---|---|---|---|---|---|---|---|
| | | Plasma Cmax (µM) | Brain Cmax (µM) | Brain/plasma ratio | Plasma Cmax (µM) | Brain Cmax (µM) | Brain/plasma ratio |
| 5 | 0.1 | 2.31 | 5.65 | 2.45 | 1.38 | 1.64 | 1.19 |
| TC3.6 | 1.04 | 6.79 | 3.46 | 0.51 | 0.86 | 0.37 | 0.43 |

TABLE 4

Comparison of PDE7 Cmax/IC$_{50}$ ratios of compounds 5 and TC3.6 after intraperitoneal or oral administration in mice.

| Comp. | Intraperitoneal administration Cmax/PDE7 IC$_{50}$ ratio | | Oral administration Cmax/PDE7 IC$_{50}$ ratio | |
|---|---|---|---|---|
| | Plasma | Brain | Plasma | Brain |
| 5 | 23.1 | 56.5 | 13.8 | 16.4 |
| TC3.6 | 6.53 | 3.33 | 0.83 | 0.36 |

The invention claimed is:

1. A pharmaceutical composition comprising a compound selected from the group consisting of:
    (i) 2-Cyclohexylmethylthio-3-phenyl-4-oxo-3,4-dihydroquinazolin;
    (ii) 3-(2-Bromophenyl)-2-cyclohexylmethylthio-4-oxo-3,4-dihydroquinazoline;
    (iii) 3-Phenyl-2-neopentylthio-4-oxo-3,4-dihydroquinazoline;
    (iv) 3-(2,6-Difluorophenyl)-8-methyl-2-neopentylthio-4-oxo-3,4-dihydroquinazoline;
    (v) 8-Chloro-3-phenyl-2-neopentylthio-4-oxo-3,4-dihydroquinazoline;
    (vi) 3-(2-Bromophenyl)-2-cyclopropylmethylthio-4-oxo-3,4-dihydroquinazoline;
    (vii) 2-Cyclopropylmethylthio-3-(2,6-difluorophenyl)-8-methyl-4-oxo-3,4-dihydroquinazoline; and
    (viii) 3-Phenyl-2-(2-naphthylmethylthio)-4-oxo-3,4-dihydroquinazoline;
    or a salt or an isomer thereof.

2. The pharmaceutical composition according to claim 1, wherein the composition is in solid form or in aqueous suspension.

3. A pharmaceutical composition according to claim 1, comprising an acceptable solvate.

4. A compound of formula selected from the group consisting of:
    (i) 2-Cyclohexylmethylthio-3-phenyl-4-oxo-3,4-dihydroquinazolin;
    (ii) 3-(2-Bromophenyl)-2-cyclohexylmethylthio-4-oxo-3,4-dihydroquinazoline;
    (iii) 3-Phenyl-2-neopentylthio-4-oxo-3,4-dihydroquinazoline;
    (iv) 3-(2,6-Difluorophenyl)-8-methyl-2-neopentylthio-4-oxo-3,4-dihydroquinazoline;
    (v) 8-Chloro-3-phenyl-2-neopentylthio-4-oxo-3,4-dihydroquinazoline;
    (vi) 3-(2-Bromophenyl)-2-cyclopropylmethylthio-4-oxo-3,4-dihydroquinazoline;
    (vii) 2-Cyclopropylmethylthio-3-(2,6-difluorophenyl)-8-methyl-4-oxo-3,4-dihydroquinazoline; and
    (viii) 3-Phenyl-2-(2-naphthylmethylthio)-4-oxo-3,4-dihydroquinazoline.

* * * * *